(12) United States Patent
Weissman et al.

(10) Patent No.: US 6,924,104 B2
(45) Date of Patent: Aug. 2, 2005

(54) METHODS FOR IDENTIFYING GENES ASSOCIATED WITH DISEASES OR SPECIFIC PHENOTYPES

(75) Inventors: Sherman Weissman, New Haven, CT (US); Xinghua Pan, West Haven, CT (US)

(73) Assignee: Yale University, New Haven, CT (US)

( * ) Notice: Subject to any disclaimer, the term of this patent is extended or adjusted under 35 U.S.C. 154(b) by 27 days.

(21) Appl. No.: 09/984,348

(22) Filed: Oct. 29, 2001

(65) Prior Publication Data

US 2002/0150919 A1 Oct. 17, 2002

Related U.S. Application Data

(60) Provisional application No. 60/243,407, filed on Oct. 27, 2000.

(51) Int. Cl.[7] ............................ C12Q 1/68; C12P 19/34
(52) U.S. Cl. ......................................... 435/6; 435/91.2
(58) Field of Search ...................... 435/6, 91.1, 91.2, 435/875; 536/24.3, 24.33; 935/76, 77, 78

(56) References Cited

U.S. PATENT DOCUMENTS

| | | | |
|---|---|---|---|
| 6,150,112 A | 11/2000 | Weissman et al. | 435/6 |
| 6,235,502 B1 | 5/2001 | Weissman et al. | 435/91.1 |
| 6,287,825 B1 | 9/2001 | Weissman et al. | 435/91.2 |
| 6,346,399 B1 | 2/2002 | Weissman et al. | 435/94 |
| 6,506,562 B1 | 1/2003 | Weissman et al. | 435/6 |
| 6,576,448 B2 | 6/2003 | Weissman et al. | 435/91.2 |
| 2001/0039039 A1 | 11/2001 | Weissman et al. | 435/91.1 |

OTHER PUBLICATIONS

Vaughan et al, Genetic Analysis: Biomolecular Engineering, Elsevier Science Publishing, 14(5–6), pp. 169–175 (1999), XP004158700.

Waters et al, Journal of Biological Chemistry, 274(1), pp. 67–74 (1999), XP002230533.

Taylor et al, Genetic Analysis: Biomolecular Engineering, Elsevier Science Publishing, 14(5–6), pp. 181–186 (1999), XP004158702.

Pan et al, Proceedings of the National Academy of Sciences of the United States, 99(14), pp. 9346–9351, (2002), XP002230534.

Diatchenko et al, Proceedings of the National Academy of Sciences of the United States, 93, pp. 6025–6030, (1996), XP002911922.

Chakrabarti et al, Cancer Research, 60(14), pp. 3732–3737 (2000), XP002230535.

*Primary Examiner*—Kenneth R. Horlick
(74) *Attorney, Agent, or Firm*—Seed IP Law Group PLLC

(57) ABSTRACT

An improved method for screening genomic, cDNA, or any DNA fragments in general is described. Novel adapters are ligated to the ends of DNA fragments from two different individuals or two different pools of individuals. The DNA fragment-adapter complexes are mixed, denatured and reannealed to form homohybrid and heterohybrid DNA duplexes, which are separated based on characteristics of the adapters. Sequence differences between heterohybrids can be revealed as mismatched base pairs in the heterohybrid DNA duplex. Mismatch base pairs are discovered using genome mismatch scanning techniques that use thymine glycosylases and related enzymes that capture DNA containing mismatched base pairs. The perfectly base paired DNA or DNA containing mismatched base pairs can be further separated into homohybrids and heterohybrids using novel adapters that allow physical capture of either heterohybrid or homohybrid DNA.

47 Claims, 18 Drawing Sheets

SEQUENCE LISTING

```
<160> NUMBER OF SEQ ID NOS: 4

<210> SEQ ID NO 1
<211> LENGTH: 60
<212> TYPE: DNA
<213> ORGANISM: homo sapiens

<400> SEQUENCE: 1
ccgtggtact tacatcgaga gatccgcttg gtgtggattc acgcacgtag accgattcct    60

<210> SEQ ID NO 2
<211> LENGTH: 60
<212> TYPE: DNA
<213> ORGANISM: homo sapiens

<400> SEQUENCE: 2
aggaatcggt ctacgtgcgt gaatccacac caagcggatc tctcgatgta agtaccacgg    60

<210> SEQ ID NO 3
<211> LENGTH: 76
<212> TYPE: DNA
<213> ORGANISM: homo sapiens

<400> SEQUENCE: 3
gatccgtcga cctgcaccgt ggtacttaca tcgagagaat agcttggtgt ggattcacgc    60
acgtagaccg attcct                                                   76

<210> SEQ ID NO 4
<211> LENGTH: 76
<212> TYPE: DNA
<213> ORGANISM: homo sapiens

<400> SEQUENCE: 4
gatcaggaat cggtctacgt gcgtgaatcc acaccgagct attctctcga tgtaagtacc    60
acggtgcagg tcgacg                                                   76
```

METHODS FOR IDENTIFYING GENES ASSOCIATED WITH DISEASES OR SPECIFIC PHENOTYPES

CROSS-REFERENCE TO RELATED APPLICATIONS

This application claims the benefit of U.S. provisional application Ser. No. 60/243,407 filed Oct. 27, 2000, the disclosure of which is expressly incorporated herein.

TECHNICAL FIELD OF THE INVENTION

The field of this invention is genetic mapping, and also genetic variation or mutation screening.

This invention presents an improved method for screening single nucleotide polymorphisms/variations/mutations (SNPs) and identical sequences between two pools of genomic or cDNA or multiple genes, or within one of these pools, each pool comprising the DNA from one individual or multiple individuals. It may be used for isolating or and mapping the genes or genetic markers related to any trait such as human complex traits, simple Mendelian diseases or somatic genetic mutation. It may also be used for profiling and/identifying SNPs for any DNA or cDNA pool or between 2 pools of them.

This invention presents an improved method for screening genomic, cDNA, or any DNA fragments in general, and capturing and/or mapping genes related to any trait. DNA is digested with restriction endonucleases and adapters with novel designs are ligated onto the ends. The adapters allow improved methods to prepare heterohybrid DNA in which a DNA double helix is formed from single strands originating from two different individuals or two different pools of DNA. The methods allow for separating heterohybrids and homohybrids that are formed in the same annealing reaction and specifically recovering either the heterohybrids or the homohybrids. Sequence differences (polymorphisms) between the two individuals are revealed as base mismatches in the heterohybrid DNA duplex. The well-established method of genome mismatch scanning (GMS) makes use of heterohybrid DNA to reveal polymorphisms between the complementary strands. An improved method of GMS is shown in which thymine glycosylases and related enzymes are used to capture DNA containing the mismatched basepairs in the heterohybrid DNA. The novel adapters allow the selective amplification or physical capture of either heterohybrid or homohybrid DNA following the separation of perfectly base paired DNA or DNA containing mismatched basepairs by glycosylases or other GMS enzymes.

This invention presents an improved method for screening DNA pool(s) in general, and isolating the single nucleotide variations (SNPs)-containing DNA sequences from identical DNA sequences between two pools of DNA or within one of these pools, each pool comprising genomic, cDNA, or any other DNA fragments from one or multiple individuals. Mapping of any trait is realized by parallel analysis of resulted mismatch fragments and perfectly matched fragments from either/both heterohybrid pool between the desired trait DNA pool and its control, or/and from the homohybrid pool from the control DNA pool, via gel display, subtractive hybridization, DNA microarray hybridization, FISH, or other approach. DNA Glycosylases or other mismatch repair enzymes with similar function are employed to separate mismatch fragments from perfectly matched fragments. A series of strategies with novel designed adapters is given for specific and selective recovery and amplification of either homohybrids or the heterohybrids from the same mixture of two resources of DNA population after restriction digestion, adapter ligation, mixing, denature and reannealing.

The invention includes two related novel techniques:

1) An improved method for separating and recovering either homohybrids or heterohybrids (in which the two strands of a double helix are contributed by two different individuals) formed in an annealing reaction. The heterohybrid DNA is selectively amplified via novel adapters ligated to the ends of the DNA.
2) A method to capture those heterohybrids which contain single nucleotide sequence differences (SNPs) using DNA glycosylase(s) and other enzymes with similar functions.

BACKGROUND OF THE INVENTION

Most human traits are genetically complex, oligogenic/polygenic or multifactorial traits. This is the case for most human diseases and other medically relevant phenotypes such as drug-response.

A need exists for a method to rapidly identify the relevant genes. This will lead to improved understanding, prognosis, diagnosis, treatment, prevention, and establishment of markers for individualized medicine and development of new drugs. Complex diseases (or traits) are usually affected by two or more interacting genes. Sometimes more than 100 genes are involved, each contributing a small effect on the risk/susceptibility for the disease. Many of the related alleles appear at low frequency even in the patient population (some <10%, most <30%) since a given gene may not be absolutely required for the disease to occur. However, the related alleles will tend to occur at least at some higher frequency in the DNA of diseased individuals compared to the DNA of control subjects. These allele frequency differences form the basis for strategies to identify those genes linked to the disease.

Humans are an out-bred species. Many polymorphisms or sequence variations exist, of which may have no relation to the trait of interest. In other words, the variants exist not only between the diseased and control cohorts, but also within each group. Actually most of the human polymorphism exists within each population. So, parallel comparison of the variations between the trait population with its control population is critical when the associated genetic markers or genes is desired.

The approaches currently available for gene discovery, such as Functional cloning depending on information about the protein, and Positional cloning relying on gene position information, are mainly successful for simple Mendelian diseases. A few successful efforts have been reported on limited number of genetic markers and on some knowledge for mapping human complex traits, for example using Candidate gene approach or genome scanning with limited number of micro satellites or other markers, yet many obstacles exist. New approaches are required for complex disease gene identification.

One whole genome screening approach previously proposed, as GMS (Genomic Mismatch Screening), is a two-step method for biochemical enrichment of the regions of the genome at which two individuals share identical alleles; it is designed to map all the regions of genetic IBD (identical-by-descent) between two related individuals. First, heterohybrid DNA molecules formed by a process of solution hybridization between two genomic DNA fragment pools from two individuals are purified by a procedure based on differential restriction methylation and endonuclease digestion. A DNA methylase was used to methylate the DNA of one individual but not the DNA of the second individual. The DNAs were then mixed, denatured, and reannealed to from a mixture of heterohybrid and homohybrids DNA. This will result in hemimethylated DNA for heterohybrids that is resistant to certain restriction endonucleases. Homohybrid DNA, in contrast can be eliminated by digestion. Second, mismatch-containing hybrids formed between nonidentical alleles are eliminated by treatment with the *Escherichia coli* mismatch repair enzymes, Mut H, MutL and Mut S, which are capable of binding and modifying the base mispair-containing hybrids in the existence of "GATC" site. The remaining mismatch-free heterohybrids, representing loci at which the two individuals share identical alleles, can then be mapped in a single genome-wide hybridization step. Researches have shown that GMS can be used to mapp the regions of IBD (Identical-by-Descent) between 2 strains of yeast, mouse, or two human individuals (Nelson S F, Nature Genetics, 4:11, 1993; Mirzayans F, Am J Hum Genet, 61:111, 1997; Cheung V G, Genomics, 47: 1–6, 1998; McAllister L, Genomics, 47: 7, 1998; Cheung V G, Nature Genetics, 18: 225, 1998; Gerton J L, PNAS, 97; 11383, 1999).

The genetic analysis of this invention is based on the frequencies of single nucleotide polymorphisms (SNPs). SNPs are the most abundant, stable and evenly distributed bi-allelic polymorphisms in the human genome, and occur at the rate of $1/300$–$1/1000$ bp between 2 genome samples ($>3 \times 10^6$ SNPs) or $1/2000$ bp between 2 coding sequences (cSNPs). In human populations, about $2 \times 10^7$ SNPs are expected. As the coding regions are 2.5–5% of the genome, so the total number of cSNPs is estimated to be >2.5% ($>5 \times 10^5$ cSNPs) of the total SNPs in the human genome, an average of about 6 per gene, with about half of them resulting in non-synonymous codon usages (Collins F S, Genome Res., 1998: 8:1229–1231; Brookes A J, Gene, 1999, 234:177–186). 90% of the sequence variants in humans are SNPs. In recently years SNPs have been considered to be the best gene-mapping marker.

Different from that of GMS, the genetic analysis of this invention is based on the frequencies of single nucleotide polymorphisms (SNPs). SNPs are considered to be the best gene mapping marker in recent years with the human genome project is coming to be accomplished. SNP marker has several advantages comparing to the other previous commonly used genetic markers such as RFLP (restriction fragment length polymorphism), STR (short tandem repeats) or IBD used in GMS. SNPs are the most abundant, stable and evenly distributed bi-allelic polymorphisms in the human genome, and occur at the rate of $1/300$–$1/1000$ bp between 2 genome samples ($>3 \times 10^6$ SNPs) or $1/2000$ bp between 2 coding sequences (cSNPs). In human populations, about $2 \times 10^7$ SNPs are expected. As the coding regions are 2.5–5% of the genome, so the total number of cSNPs is estimated to be >2.5% ($>5 \times 10^5$ cSNPs) of the total SNPs in the human genome, an average of about 6 per gene, with about half of them resulting in non-synonymous codon usages (Collins F S, Genome Res., 1998: 8: 1229–1231; Brookes A J, Gene, 1999, 234: 177–186). 90% of the sequence variants in humans are SNPs.

Currently, the major technique for applying SNPs in gene mapping is SNP typing based on knowledge of the individual SNPs. Variants of approaches based on variants of mechanisms have been invented to accomplish SNP typing. These include overlapping genomic sequencing or minisequencing, olignucleotide ligation assays (OLA), primer extension assays, allele-specific oligonucleotide (ASO) hybridization, exonuclease assays or 5' nuclease assay, single base chain extension, and so on. Only some of them such as microarray techniques and mass spectrometry have the necessary features for industrial-scale SNP typing. Although these techniques succeed in some applications, few excellent examples using these techniques to map a typical complex disease have been reported. The major obstacles facing gene mapping of complex traits with SNPs are two. First, the SNPs currently or in near future available in trait mapping are too few in number, so they do not satisfy the requirement of genome coverage; second, thousands of individual samples may be required according to the theoretic prediction of geneticists. In addition, the intrinsic characteristics of the genetic complexity of complex traits and the complexity of the human genome also make the difficulties.

One approach previously proposed to use SNPs in genetic analysis is based on mixing the DNAs of two individuals together, denaturing, and then reannealing the strands back together. Therefore the DNA strands of the different individuals can base pair with each other. In this case, a mixed double stranded DNA will be formed, called a heterohybrid, in which one of the strands of the double helix is contributed by one individual, and the complementary strand is contributed by a different individual. Where the individuals have different DNA sequences (polymorphism), the strands of the heterohybrid will not form correct base pairs. Therefore, a high rate of polymorphism between the individuals will result in many mispaired bases in the heterohybrid DNA and a low rate of polymorphism will result in more perfectly matched bases. This difference forms the basis for methods to rapidly measure the diseases-related identical-by-descent (IBD) sequences. (IBD refers to sequences that individuals have in common, i.e. having low polymorphism, as a result of inheriting a trait from a common ancestor. IBD is used to associate sequences of low polymorphism to the trait.)

A class of DNA repair enzymes, MutHLS, was used to identify the mispaired bases in heterohybrid DNA. These enzymes are capable of binding and modifying base mispairs. The repair enzymes were used to remove the mispaired bases and thereby reveal the IBD sequences among two or more individuals. Such a strategy using yeast as the test organism was presented by Nelson and associates in 1993, and referred to as Genomic mismatch scanning (GMS)(Nelson S. F., et al. Nature Genetics, 1993, 4:11–18 and related subsequent papers). GMS has been modified and successfully used in screening traits related by IBD from yeast and from human chromosomes in conjunction with putative disease gene localization information. A critical step in the GMS procedure is the enrichment of heterohybrid DNA away from homohybrid DNA. A relatively complex and laborious approach was used (Nelson S. F., et al. Nature Genetics, 1993, 4:11–18; Cheung, V. G., et al. (1998) Nature Genetics, vol. 18, 224–230) that required multiple steps. A DNA methylase was used to methylate the DNA of one individual while not the methylating the DNA of the second individual. The DNAs were then mixed, denatured, and reannealed to from a mixture of heterohybrid and homohybrids DNA. This will result in hemimethylated DNA for heterohybrids that is resistant to certain restriction endonucleases. Homohybrid DNA, in contrast can be eliminated by digestion.

Some repair enzymes such as MutHLS have been used to detect the existence of mismatch-containing DNA fragments. (ref. Taylor G R, Deeble J. Genet Anal. 1999;14(5–6):181–6; Marra G, Schar P. Biochem. J. 1999;338 (Pt 1):1–13). DNA glycosylases have also been tested to detect DNA damage or mutation (Dennog C, et al. Mutat Res. 1999; 17;431(2):351–9; Gualillo O, et al. Vaughan P, et al. Genet Anal. 1999; 14(5–6):169–75).

DNA glycosylases have also been tested to detect DNA damage or mutation (Dennog C, et al. Mutat Res. 1999; 17;431(2):351–9; Gualillo O, et al. Vaughan P, et al. Genet Anal. 1999; 14(5–6):169–75). Most of the researches relaying on these MRS enzymes are focused on the detection of signal to noise ratio of the test sample comparing to control sample regarding one or a limit number of known SNPs-containing fregments, so as to determine whether or not any of these potential SNPs really exist, or to detect the mutation in one or a limited number of known genes. No report was found to apply this kind of enzyme to separate mismatch fragment pool from perfectly matched fragment pool.

SUMMARY OF THE INVENTION

The strategy involves several categories of new techniques:

Adapter and primer designs that allow specific amplification of either heterohybrid or homohybrid DNA. Heterohybrid is defined here as double-stranded DNA formed by annealing together complementary strands from two different individuals. For example, the DNA of two patients sharing a disease in common, can be mixed together, denatured by heating, and reannealed by cooling. In some cases, the two complementary DNA strands of one individual reanneal back together (referred to as a homohybrid). There is a need to separate the useful heterohybrid DNA form the homohybrids. Novel adapters are presented here that allow the specific amplification or capture of heterohybrids. The enriched heterohybrid DNA can then be used in polymorphism analysis. The degree of sequence polymorphism between the individuals is reflected as mismatched base pairs in the heterohybrid.

Sensitive and specific capturing of heterohybrids containing SNPs with DNA glycosylases. Glycosylases are DNA repair enzymes that bind and modify DNA containing mismatched base pairs. They can be used to separate DNA fragments with high polymorphism (resulting in base mispairs in heterohybrids or in homohybrids), from fragments with low polymorphism. The use of glycosylases in capturing DNA mismatches is an improvement over methods currently in use.

This invention is based on a parallel analysis on the products of the separately enriched SNP mismatch fragment or perfectly matched (PM) from heterohybrids or either one of the two homohybrids via DNA microarray hybridization, gel display, subtractive hybridization, FISH (fluorescent in situ hybridization), or other techniques. These heterohybrids and homohybrids are formed by mixing, denaturing and reannealling the DNA pools from the trait population and its control pool that are previously separately digested, and ligated to a pair of differentially designed heterohybrid-directed adapters (HeD adapter) and their derivations. The heterohybrids and homohybrids are separately recovered from one general pot of above mixture by the triple-recovery strategy (TRS), which is usually followed the separation of PM fragments from SNP fragments by DNA Glycosylase or other enzymes with similar functions. The gene mapping of the trait, or the SNPs or/and IBDs profiling of any given DNA pool will be obtained from the output analysis. (FIG. 1)

The DNA pool or DNA sample is the starting material for the current approach, which here refers to either genomic or cDNA or a collection of a number of genes from one individual or a population of many individuals (pooling strategy). For example, the pool of genomic DNA mixture from many patients sharing a disease or any trait in common, and its control pool from a number of control individuals without this disease or trait, can be separately digested by a restriction enzyme, ligated to differentially designed adapters. Then these two constructs are mixed together, denatured and reannealed. In some cases, two complementary DNA strands of one pool, either from the same original duplex matched or its homolouous chromosome of the same or different individual of the same pool, may reanneal together as a DNA duplex, which is referred to as a homohybrid. In other cases, two complementary strands from different DNA pools may anneal together and form another kind of DNA duplex, which is referred as a Heterohybrid. Obviously, both homohybrid and heterohybrid can be either perfect matched duplex or mismatched duplex, and most of the mismatches are produced from single nucleotide polymorphisms, called as SNP segment or SNP fragment (if digested by a restriction enzyme), including SNP homohybrid and SNP heterohybrid. DNA Glycosylases and similar enzymes are used to separate and enrich SNP mismatch fragments from perfectly matched fragments. The SNP segments between a trait DNA pool and its control, when quantitatively or qualitatively excluded the neutral SNPs within the control pool, are associated with the target traits. This exclusion or parallel analysis is important is important because most of human genetic polymorphisms exists within a population between rather than between two populations, and the "net" genetic polymorphisms that may be associated with a given human traits are very limited.

The enriched and separated perfectly matched fragments (PM segment or PM fragments, including PM homohybrids and PM heterohybrids)are taken as a result of heritage from a common ancestor and are referred as IBD segment or IBD fragment when they are derived from the same pool (i.e. PM homohybrids). It is certain that single base pair mismatches will be present in sufficiently large (ex. 2 kb–20 kb) DNA hybrids formed between allelic sequences that are not IBD. In other words, the perfectly matched fragments of hybrids from two related individuals, given it is long enough, can be regarded as IBD segments; but for a short fragment, the perfectly matched fragments of hybrids may be Identical-by-State (IBS segment or IBS fragment). The IBD fragments sharing among the different individuals with the same trait can be taken as a second information for the genetic mapping of the given trait in addition the SNP information. The IBD fragments or even the IBS fragments between the pool of trait and its control can also be quantitatively or qualitatively taken as a control information for genetic mapping of the trait. When SNP information is desired, a frequently cutting restriction enzyme such as Sau3AI or a combination of a few of frequently cut enzymes is the choice; in this case, the IBS information may come out from the same one procedure as IBD. When IBD information is desired, a rare cutting restriction enzyme such as PstI is the choice, and genomic DNA is necessary; in this case, the SNP information are unavailable or very incomplete.

This invention involves additional categories of new techniques and a new strategy for analysis of the output fragment pools:

1. A method for separating and amplifying either one of the two homohybrids or the heterohybrids from the mixture following by mixing two pools, denature and annealing.

Triple-Recovery-Strategy based on HeD (Heterohybroid-directed) adapters and their derivations allows specific amplification of either heterohybrids or one of the two homohybrids. Several strategies are given for this purpose.

2. A method to separate the SNP fragments from PM fragments with high specificity and sensitivity by the employment of DNA glycosylase(s) and other enzymes with similar functions, and collect these two DNA fragment pools separately.

DNA Glycosylases are DNA repair enzymes that bind and modify DNA containing any one of 4 classes of single nucleotide mismatches (i.e. G/T and C/A, G/A and C/T, GlG and C/C, and T/T and A/A) with a high with high specificity and sensitivity. They modify the mismatched base(s) and result an abasic site, which can be tightly bound by these enzymes or other chemical or physical approach.

3. A strategy of combining employment of the two approaches said above and other necessary designs for a parallel analysis and comparison of the output fragment pools following the treatment above, and obtaining the SNP information as well as identical sequences (IBDs or IBSs) information in terms of their nature, frequency, localization and finally the genetic and possible physical mapping of the target trait. The analysis techniques include parallel DNA microarray hybridization, gel display, subtractive hybridization, FISH (fluorescent in situ hybridization), or other techniques with the output fragments as the probes.

Figure 1:
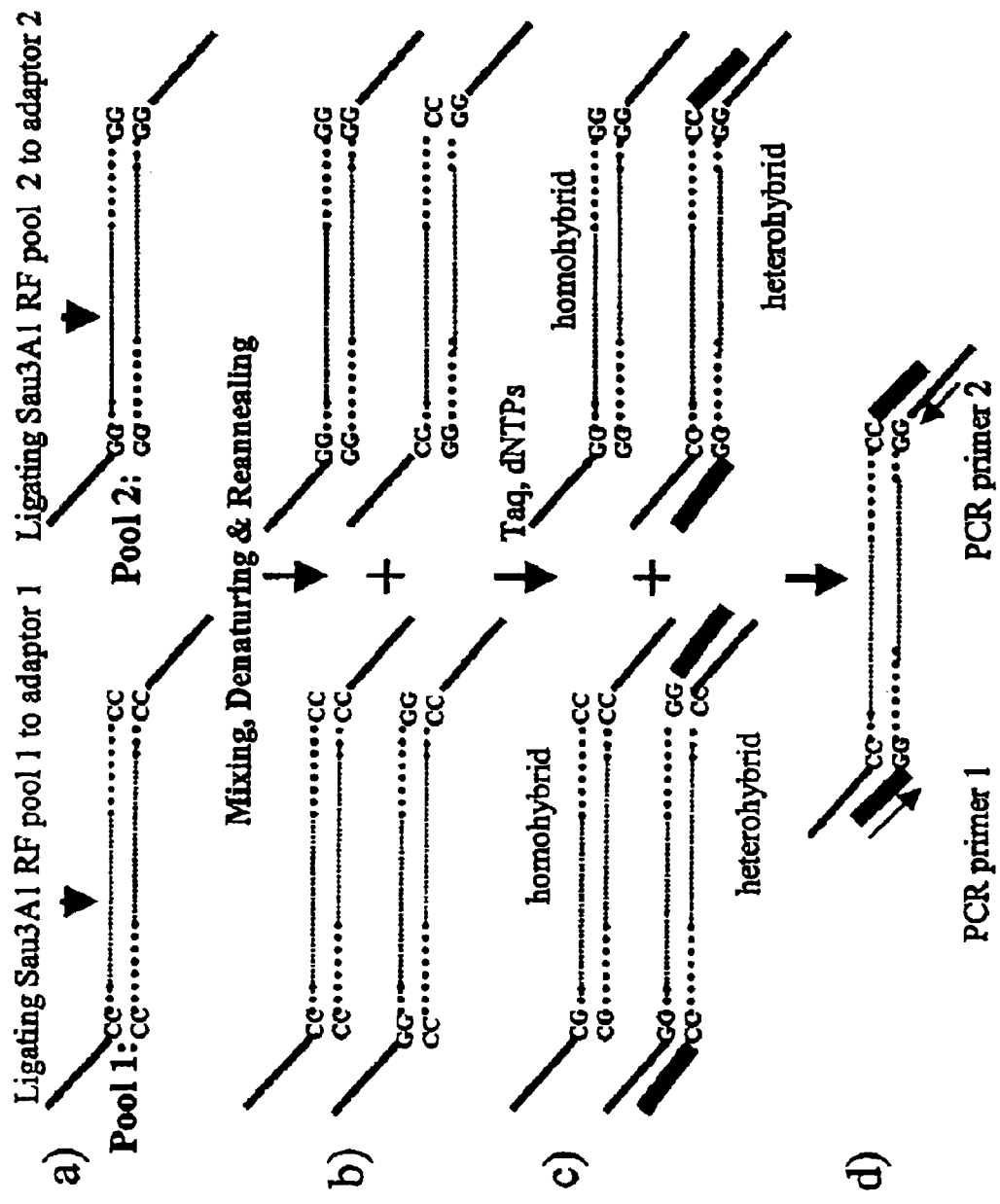
FIG. 1 illustrates selective recovery of AB in one pot by employment of a 3' Exonuclease and Smart adaptor.

Because two primers are required for the recovery of the heterohybrids while only one primer corresponding to the original RF pool is required for the recovery of one source of homohybrids, the heterohybrids will be not co-recovered when one source of homohybrids is recovered. But when heterohybrids alone is desired to recover, 2 primers are employed and the homohybrid adapters (esp. their distal part) are necessary to be removed, for which 4 possible classes of strategies (TRS 1–8, they may be combined with each other) are given.

When selectively methylation RE sites are introduced in a modified HeD adaptors, three classes of strategies are given here, which take advantage of the fact that some REs are sensitive or resistance to methylation to differently separate homohybrids from heterohybrids. When physical-chemical methods are employed, any adapter attached to two different handling groups for two pools may be suitable for selective recovery of the desired AA, BB or AB from one pot of DNA mixture. The amplicon may not be used for direct sequencing if a regular duplex adapter is used to ligate to the original RF pools.

The resultant construct has no long single strand part that may disturb the activities of MRS enzyme such as glacosylase binding specifically to SNP fragments. If an HeD adapter is used, the constructs have different sequences at two ends of a heterohybrid, but the same sequences at two ends of a homohybrid.

The fragment pools recovered/enriched in this way are suitable to be taken as probes for further analysis such as applying into microarrays, FISH, and other SNP typing or gene mapping techniques. If regular full duplex adapter is used instead of HeD adapters/derivations, the heterohybrids may not be direct sequenced or the two kinds of homohybrids may not be able to be separated from each other.

DNA glycosylase or other methods are employed when it is desired to separate SNP fragments from perfectly matched fragments. It is not an essential step for the triple-recovery strategies.

DETAILED DESCRIPTION OF THE INVENTION

The goal of this invention is to enrich DNA sequences that are related to a disease or any other phenotype of interest. Restriction endonuclease fragments of DNA from two individuals or two pools of multiple individuals are mixed together. By melting and then reannealing it is possible to form a heterohybrid DNA double helix that contains the DNA strands of two different individuals. In some cases, the strands of DNA from a single individual may reanneal back together regenerating the original homohybrids. ("Homohybrid" is defined here to mean a double helix containing DNA strands derived from a single individual in contrast to a heterohybrid).

In the present invention, we propose the use of novel adapters that allow an improved method for selectively amplifying heterohybrid DNA without the need for methylation or digestion with restriction endonucleases. The adapters also have the advantage of resulting in an amplification of the desired heterohybrids rather than a simple enrichment away from homohybrids but with no net amplification of heterohybrid DNA.

Adapters may be Y shaped adapters, which are made up of two single-stranded DNA fragments. The two single-stranded DNA fragments of the Y shaped adapter have a region of complementarity at one end that anneals the two strands, and a region of non-complementary at the opposite end that does not anneal. These complementary and non-complementary ends give the adapters their Y shape.

The complementary end allows the adapters to ligate to the ends of other DNA fragments, such as restriction enzyme digested DNA. The complementary end may be blunt ended, or have a 5' or 3' overhang, depending on the DNA fragments to which the adapters are ligated. The complementary end may also be of any suitable length. The length of the complementary end can be 1, 2, 5, 10, 15, 20, 25, 30, 40, or 50 nucleotides.

The complementary end may also have features that promote the selective amplification or recovery of homohybrid or heterohybrid DNA. The complementary end of the Y shaped adapters may have adjacent methylation-sensitive restriction endonuclease recognition sites. The sites on the Y shaped adapters may be selectively methylated such that restriction endonucleases that are sensitive to DNA methylation can be used to cleave and specifically remove the homohybrids or heterohybrids. An example of a restriction enzyme that requires methylation of its recognition site to cleave DNA is DpnI. Restriction enzymes that will only cleave in the absence of methylation include MboI, MboII, ScrFI, DpnII and ApaI. AluI is also sensitive to the methylation status of DNA. Those of skill in the art will readily recognize other methylation sensitive restriction endonucleases.

The complementary end of the Y shaped adapter may also promote the selective amplification or recovery of homohybrid or heterohybrid DNA by possessing the site for a restriction endonuclease that cuts only one strand of a double stranded DNA molecule. An example of a restriction endonuclease that cleaves only one strand of a double-stranded DNA molecule is N.BstNB1. The recognition site for the restriction endonuclease can be between 1 and 50, 1 and 45, 1 and 40, 1 and 36, 1 and 30, 1 and 25, 1 and 20, 1 and 15, 1 and 10, and 1 and 5 nucleotides of the 3' terminal sequence of the non-complementary end of the Y shaped adapter and is within the complementary end of the Y shaped adapter.

The non-complementary end of the Y shaped adapters comprises the two non-annealed strands of DNA, which are the strands with a 5' terminal sequence and the 3' terminal sequence. The sequences may be of any length. Typically the non-complementary 5' terminal sequence is 1, 2, 5, 10, 15, 20, 25, 30, 40, or 50 nucleotides in length. Typically the non-complementary 3' terminal sequence is 1, 2, 5, 10, 15, 20, 25, 30, 40, or 49 nucleotides in length. The 5' terminal sequence and the 3' terminal sequence may also be of different lengths. Preferably, the 5' terminal sequence of the Y shaped adapter is longer than the 3' terminal sequence of a Y shaped adapter.

The non-complementary ends of the Y shaped adapters also have unique features that allow the selective amplification or recovery of heterohybrid or homohybrid DNA molecules. A first Y shaped adapter with a 5' terminal end that is longer than the 3' terminal end may be annealed to a first DNA sample and a second Y shaped adapter that has a 5' terminal end that is longer than the 3' terminal end may be annealed to a second DNA sample. The 5' terminal end of the first Y shaped adapter can be complementary to the 3' terminal end of the second Y shaped adapter and the 5' terminal end of the second Y shaped adapter can be complementary to the 3' terminal end of the first Y shaped adapter. Heterohybrid DNA formed from DNA pools ligated to one or the other of these Y shaped adapters can be selectively recovered by extending the 3' terminal ends and amplifying. Amplification may be carried out by any means known in the art, such as polymerase chain reaction or rolling circle amplification.

The non-complementary ends of the Y shaped adapters may also encode restriction enzyme sites for restriction enzymes that cleave double stranded DNA. These restriction enzyme cleavage sites are preferably in the 5' terminal sequence of the Y shaped adapter.

Selective Amplification of Heterohybrids or Homohybrids Formed in a Single Annealing Reaction.

The first step of the invention is to selectively amplify the heterohybrids while eliminating the homohybrids. Two pools of patient DNA are formed, each pool comprising DNA of a different individual or a mixture from multiple individuals. (FIG. 1, pool 1, and pool 2). Pool 1 DNA is ligated to "Y shaped" adapters that are complementary to the ends of the restriction endonuclease digested DNA.

In this example, the 3' recessed end of the Y adapter ends with the bases CC which form a mismatch with two corresponding Cs in the other strand (FIG. 1a). Pool 2 DNA is ligated to "Y shaped" adapters that contain a recessed 3' GG end that is mismatched with two corresponding Gs in the other strand. The two patient DNA pools are mixed together, denatured and reannealed. Any homohybrid DNA formed will still contain either the CC or GG mismatch (FIG. 1b). The base mismatches prevent the recessed 3' arm from being filled in by a DNA polymerase that lacks a 3'–5' exonuclease proofreading activity such as Taq DNA polymerase (FIG. 1c). For any heterohybrid formed, the recessed 3' arm will now be correctly base paired with the complementary strand (forming either CC base paired with GG, or GG base paired with CC). The heterohybrid recessed 3' ends can be filled in by DNA polymerase and the four dNTPs (FIG. 1c bold lines). The method is not restricted to the 3' CC ends in this example, but can be carried out with any combination of bases that form a recessed 3' adapter end that is mismatched in homohybrids, and matched in heterohybrids. There are numerous ways to selectively amplify the heterohybrids once their recessed ends are filled in. For example, PCR primers can be designed that are only functional if the ends are filled in (FIG. 1d, primer 1 and 2). Therefore, only heterohybrids will be amplified while homohybrids will not anneal to the PCR primers.

In each of the examples shown (FIGS. 1–7), the goal is to be able to selectively separate 3 fractions that are formed in a single annealing reaction (referred to as a "single pot"). The 3 fractions are referred to as M, BB, and AB which represent the homohybrid obtained from one individual or DNA pool, the homohybrid obtained from the second individual or DNA pool, and the heterohybrids respectively.

An alternative strategy to that shown in FIG. 1 that allows recovery of homohybrids instead of heterohybrids is to fill in the ends with a DNA polymerase that possesses a 3'-5' exonuclease proofreading activity. This will allow the mismatched 3' ends of the homohybrids to be repaired and filled in. Suitable polymerases include Vent DNA polymerase, Pfu DNA polymerase, Klenow fragment of DNA polymerase I, E. coli polymerase I, and T4 DNA polymerase. The homohybrids can be distinguished form the heterohybrids by, for example, filling in the ends with normal nucleotides using the polymerase lacking proofreading activity, and then with modified nucleotides using the proofreading polymerase. Suitable polymerases include Taq polymerase, Tth polymerase, eukaryotic DNA polymerase α, and 3'-5' exominus Klenow DNA polymerase. For example, if the homohybrids are filled in with biotin containing nucleotides, they can be separated from heterohybrids with streptavidin or avidin attached to a bead of column matrix. If the homohybrids are filled in with nucleotides labeled with antigen, they can be separated from heterohybrids with an antibody specific for the antigen. If the homohybrids are filled in with nucleotides labeled with protein A, they can be separated from heterohybrids with an antibody. Other acceptable capture moieties and affinity reagents are known in the art. Also, filling in the ends of the homohybrids with methylated dATP, and in the case where an appropriate restriction endonuclease site such as DpnI is located on the adapter would allow the specific digestion of homohybrids and subsequent capture or amplification of the remaining heterohybrids.

Figure 2:
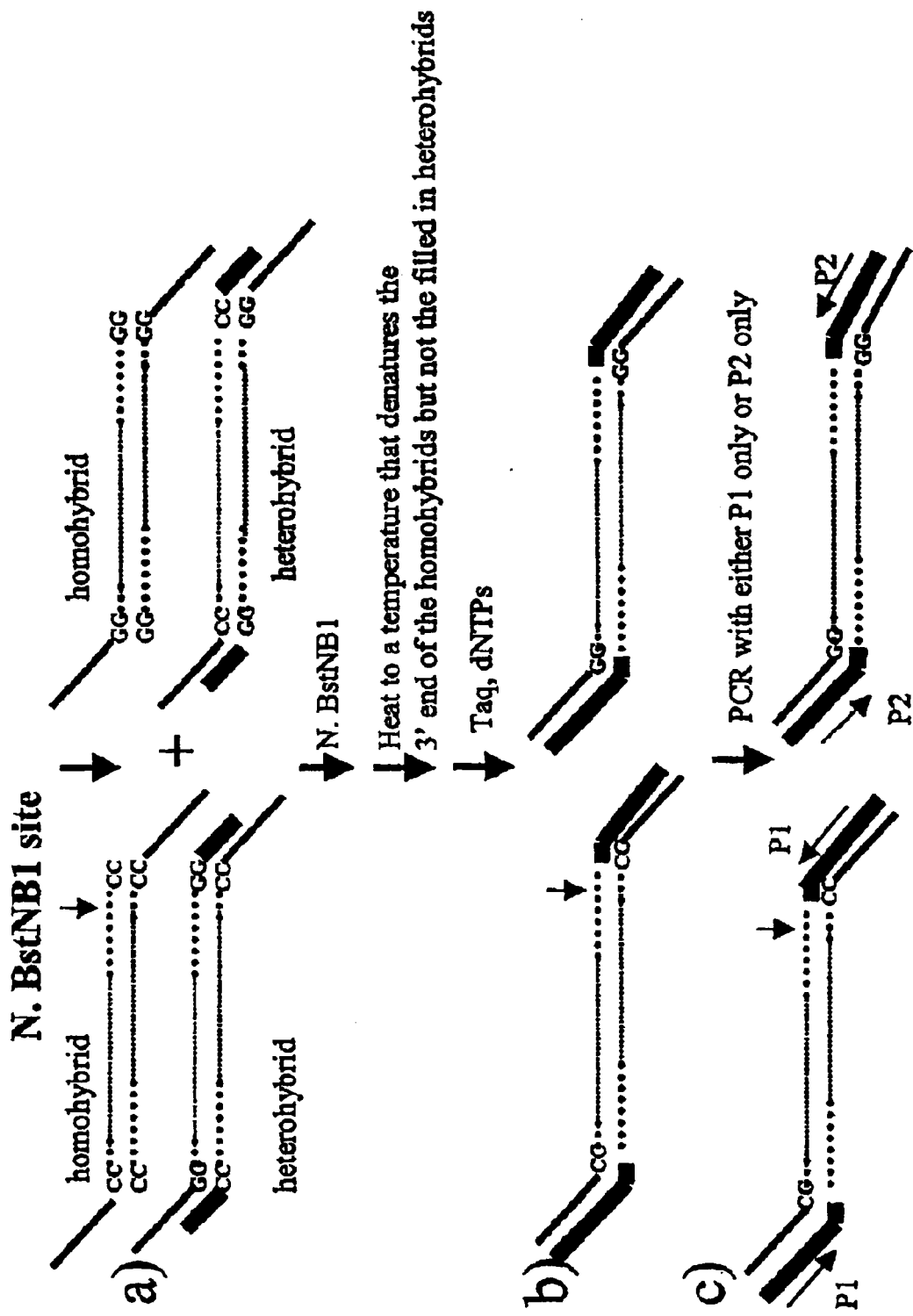
FIG. 2 illustrates selective amplification of homohybrids in one pot by employment of a N. BstNB1 site in Smart adaptor.

An alternative way to distinguish heterohybrids from homohybrids is to use a restriction endonuclease capable of nicking only one strand of the DNA such as Bst NB1 (FIG. 2). The first step is the same as in FIG. 1. The 3' recessed end of the heterohybrids are filled in by a DNA polymerase lacking proofreading activity. The homohybrids cannot be filled in due to the mismatched 3' recessed ends. However, in this example, the ends are then cut with the restriction endonuclease generating a nick as indicated. It will be possible to heat the DNA to a temperature that causes the 3' ends of the homohybrids to dissociate. Because the 3' ends of the heterohybrids have be extended in the fill in reaction, they will remain annealed at an appropriate temperature. The temperature can be at any level that allows the dissociation of the unextended 3' ends but not the extended ends. Treatment of the DNA with a ligase will close the nick in the heterohybrids. The homohybrids can be amplified by carrying out PCR with only primer 1 to obtain one homohybrid, or only primer 2 to obtain the other possible homohybrid (FIG. 2c). This distinguishes the homohybrids form heterohybrids that require both primer 1 and 2 for PCR (see FIG. 1d).

Figure 3:
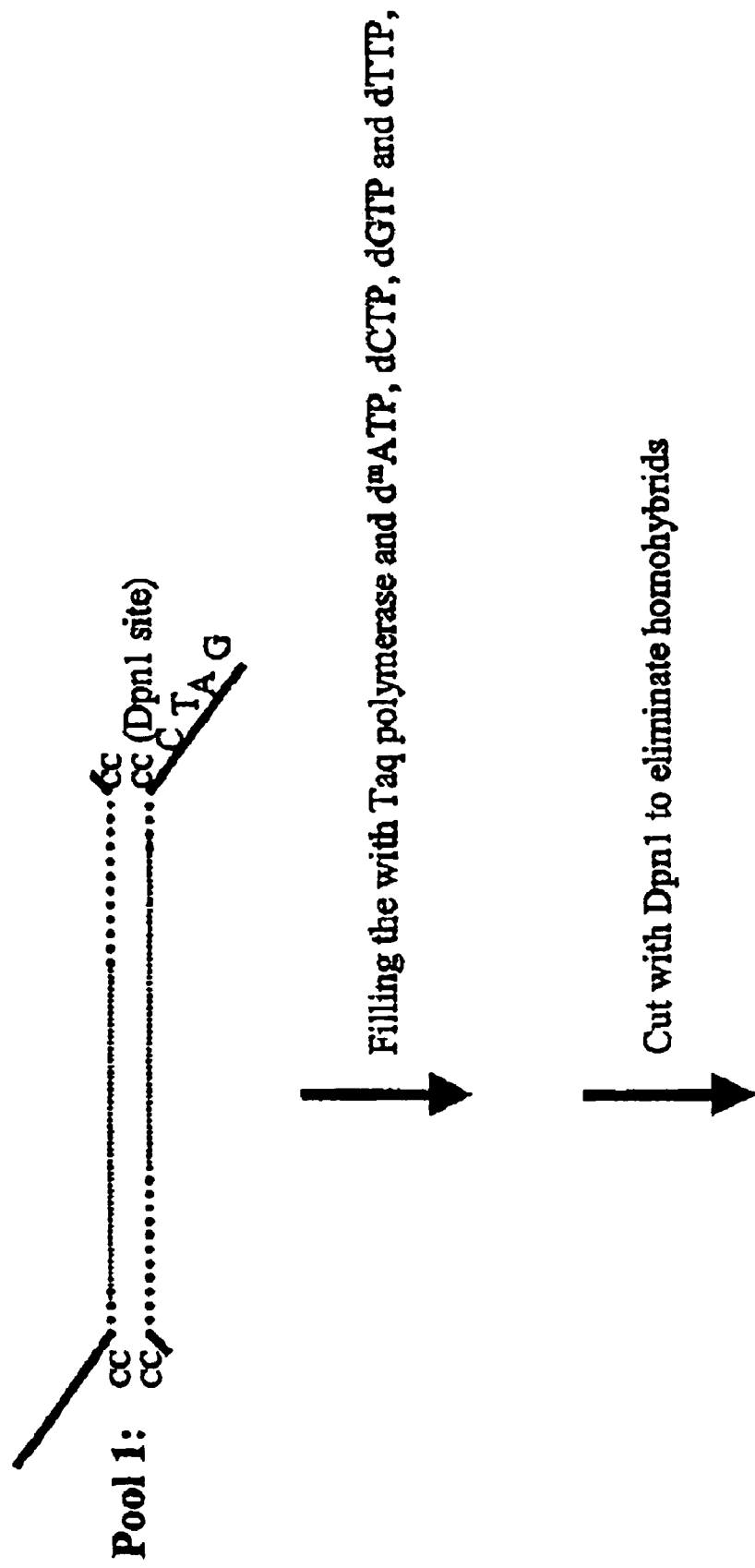
FIG. 3 illustrates the use of DpnI to receover heterohybrids.

Another method uses adapters containing the recognition sequence for restriction endonucleases such as DpnI that require methylated bases (FIG. 3). The first steps are identical to FIGS. 1a–c with normal dNTPs being used to fill in the Y shaped adapters in a first 3' end extension reaction. Bst NB1, or a similar enzyme that nicks a single strand, is then used to remove the mismatched 3' end of the adapter as in FIG. 2. With the mismatched 3' end now removed, a DNA polymerase can be used in a second extension reaction this time using methylated dATP. In this example, both homohybrids will be cut by Dpn1 which recognized the methylated A. Heterohybrids will not be cut and can therefore be selectively amplified or captured by methods described for FIG. 1.

Figure 4:
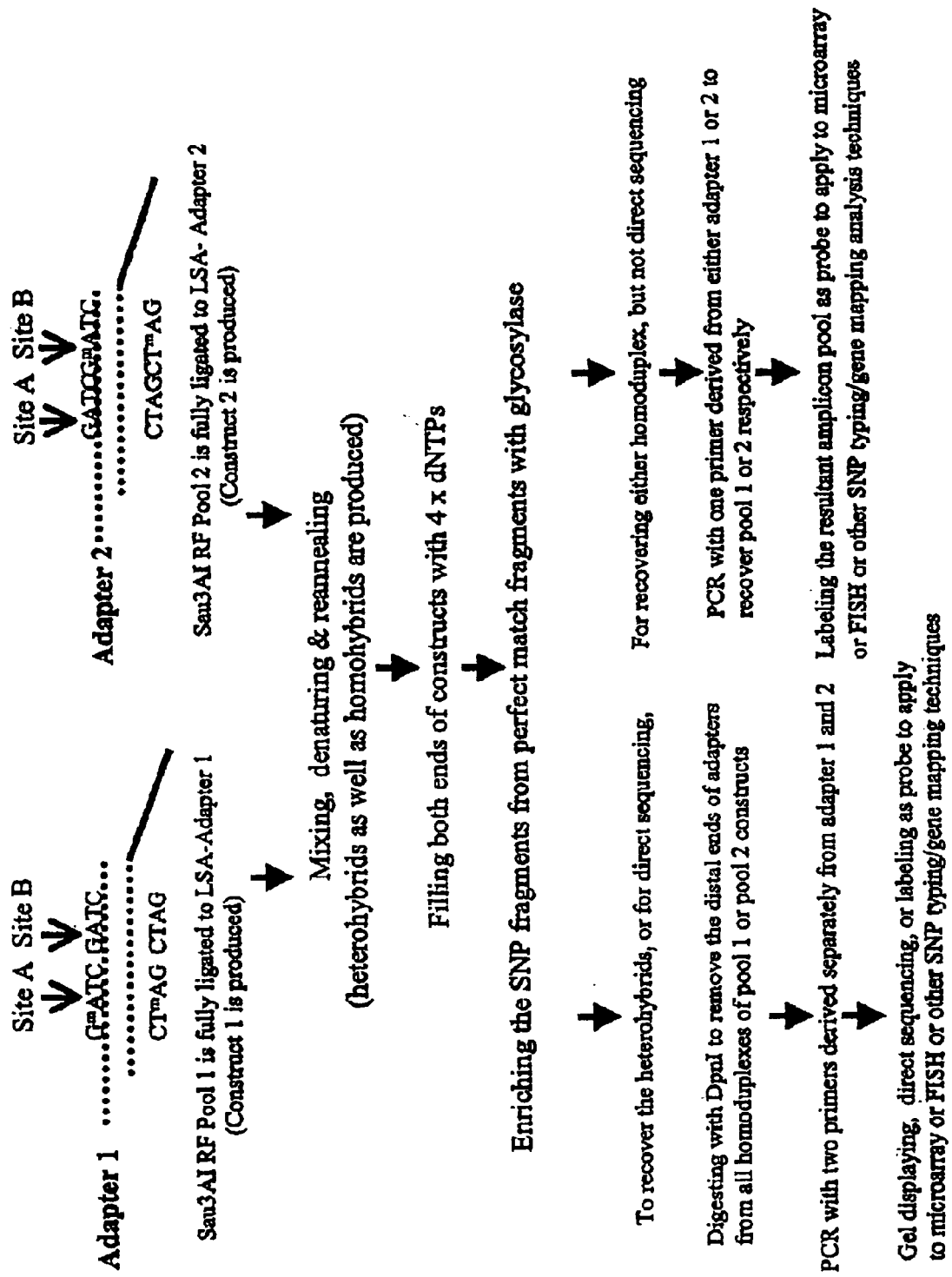
FIG. 4 illustrates selective recovery of AA, BB or AB in one pot based on DpnI site of selectively methylated LSA-adapter.
Figure 5:
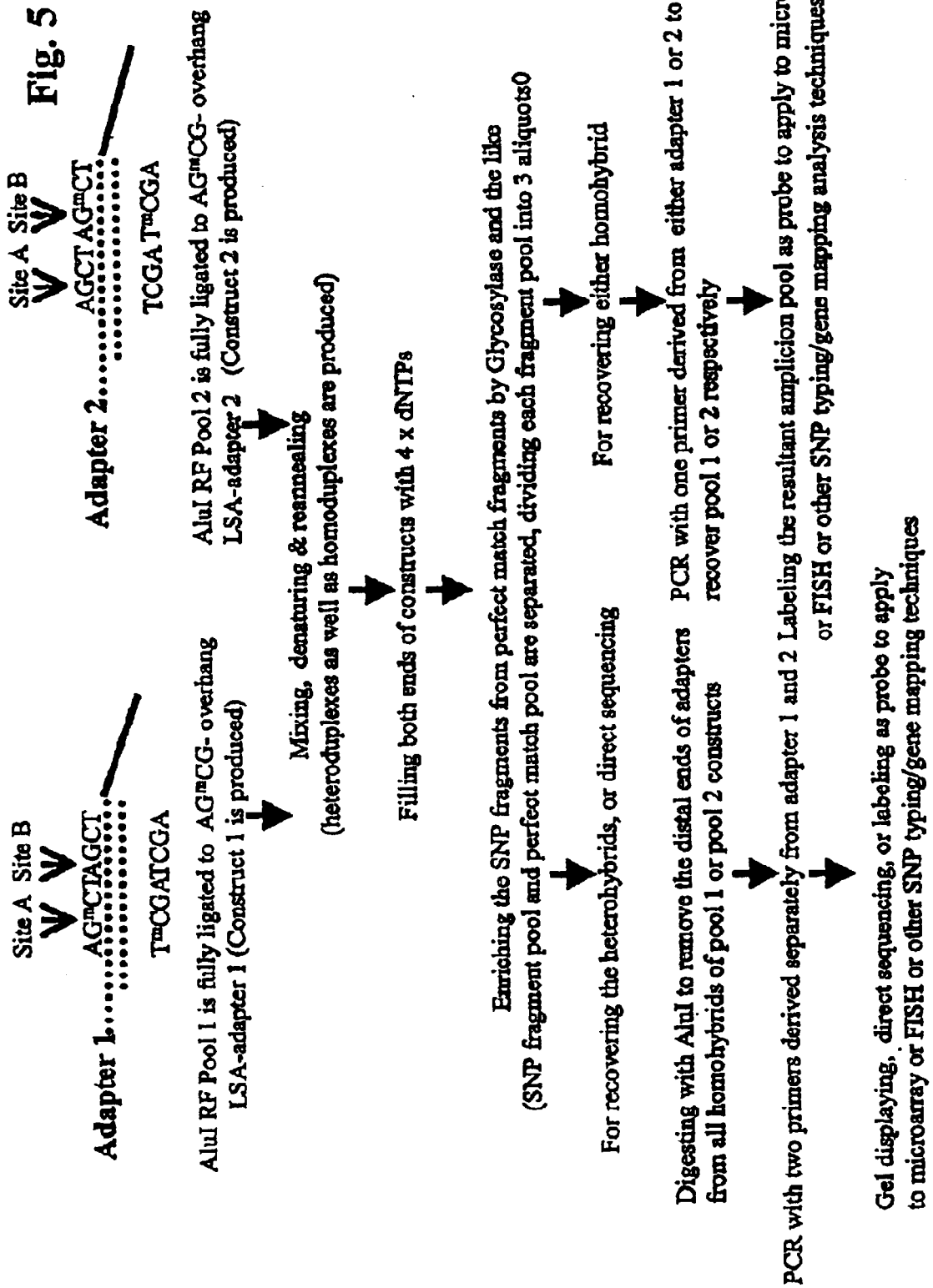
FIG. 5 illustrates selective recovery of AA, BB or AB in one pot based on AluI site of selectively methylated LSA-adapter. AluI cuts off Site B of construct 1 homoduplex, and site A of construct 2 homoduplex, but it does not cut heteroduplex, which is composed 1 strand from construct 1 and 1 strand from construct 2, and both Sites A and B are hemi-methylated. When the RE pools are prepared by Sau3AI or other REs, they should be treated by AluI methylase before they are ligated to the adapters, and no AG$^m$CT overhang is required for the adapter. Other REs such as TaqI may replace AluI, Sites A and B in the adapter and the cutting/methylation enzymes are also changed according to the REs used.
Figure 6:
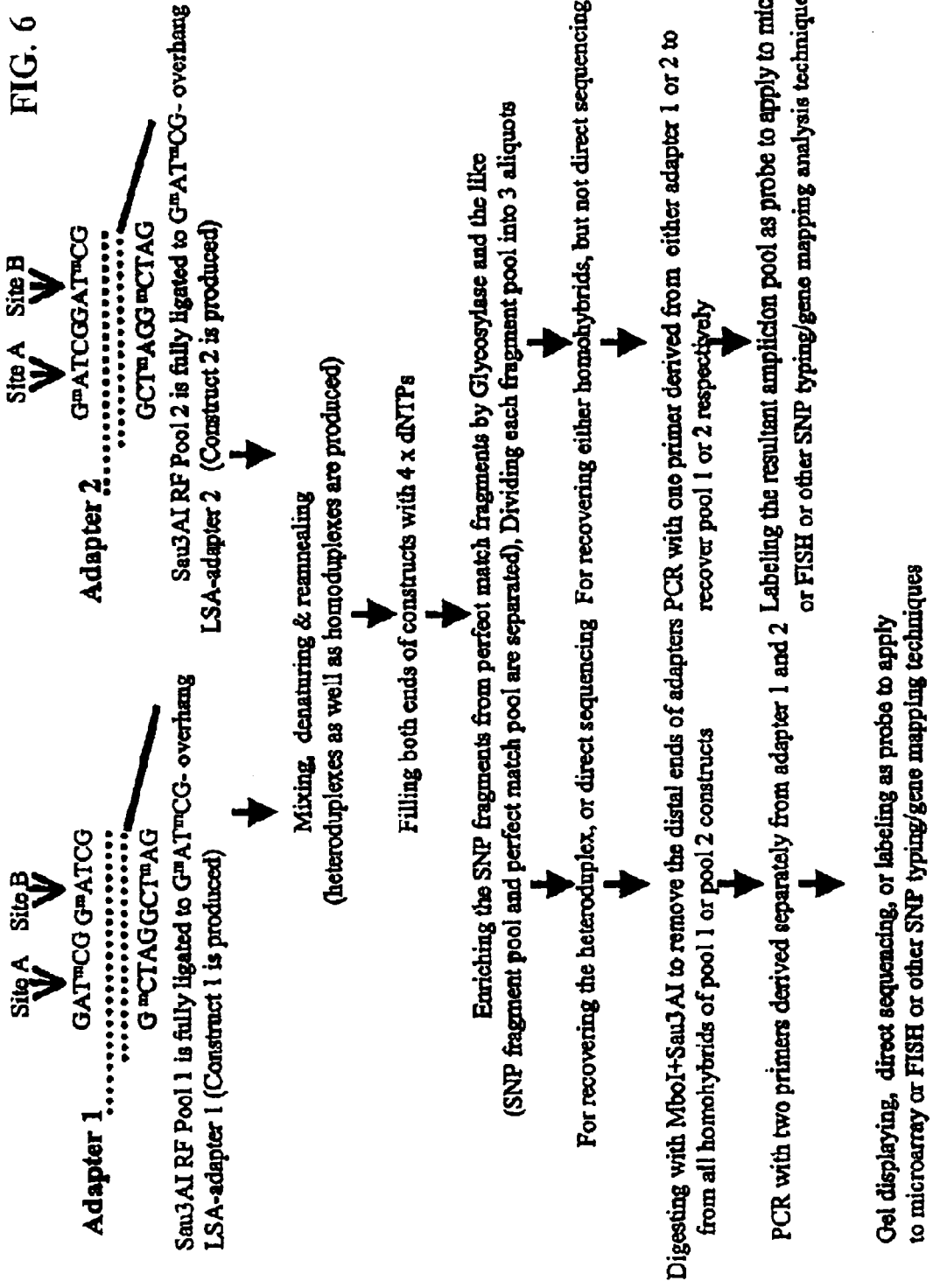
FIG. 6 illustrates selective recovery of AA, BB or AB in one pot based on MboI/Sau3AI site of selectively methylatede LSA-adapter. MboI cuts off Site A of construct 1 homoduplex; Sau3AI cuts off Site B of construct 2 homoduplex. Heteroduplex are not cut by any of two restriction enzymes (REs). G$^m$AT$^m$CG-overhang adapter is used to prevent the ligation site from being cut by either of the two REs. Other RE pairs with similar features of MboI+Sau3AI may be used to replace MboI+Sau3AI.

FIG. 4 shows another example using the recognition sequence for Dpn1, however this strategy will work for any restriction endonuclease that recognizes methylated bases. Only homohybrids will be digested by Dpn1. Heterohybrids will not be digested. FIGS. 5 and 6 show additional strategies to obtain either homohybrids or heterohybrids from the same annealing reaction. In these examples, heterohybrids can be selectively amplified using both PCR primers and it can be used directly in DNA sequencing reactions. To recover either one of the possible homohybrids (for example, one from one patient and the other from another patient) the single PCR primer is used that corresponds to the adapter ligated to the sample. In FIG. 6 MboI cuts off Site A of construct 1 homoduplex, Sau3AI cuts off site B of construct 2 homoduplex. Heteroduplex are not cut by any of the restriction enzymes (REs). G$^m$AT $^m$CG- overhang adapter is used to prevent the ligation site from cutting by either of the two REs. Other RE pair with similar features of MboI+Sau3AI may be used to replace MboI+Sau3AI.

Figure 7:
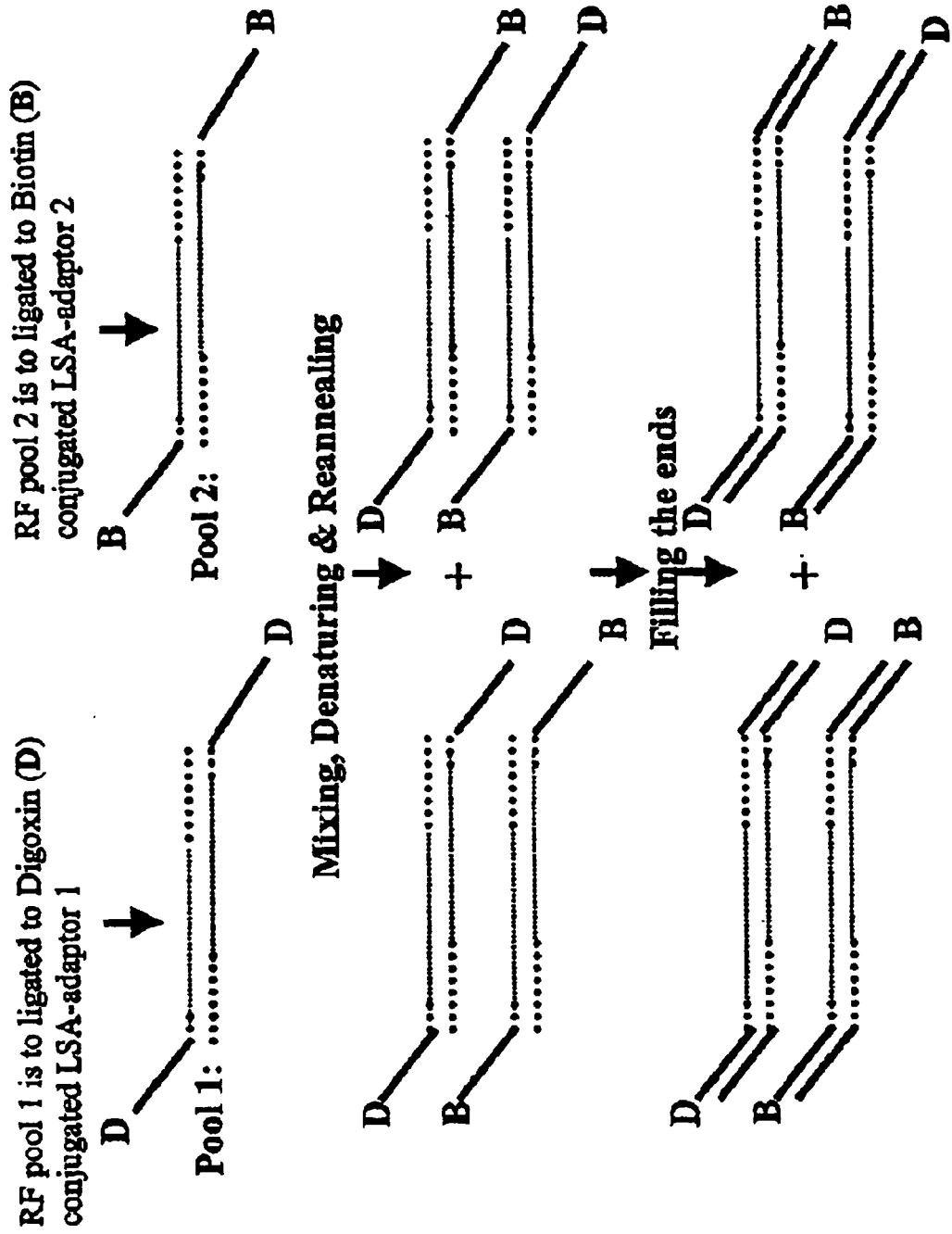
FIG. 7 illustrates selective recovery of AA, BB or AB in one pot with physical-chemical tool.
Figure 8:
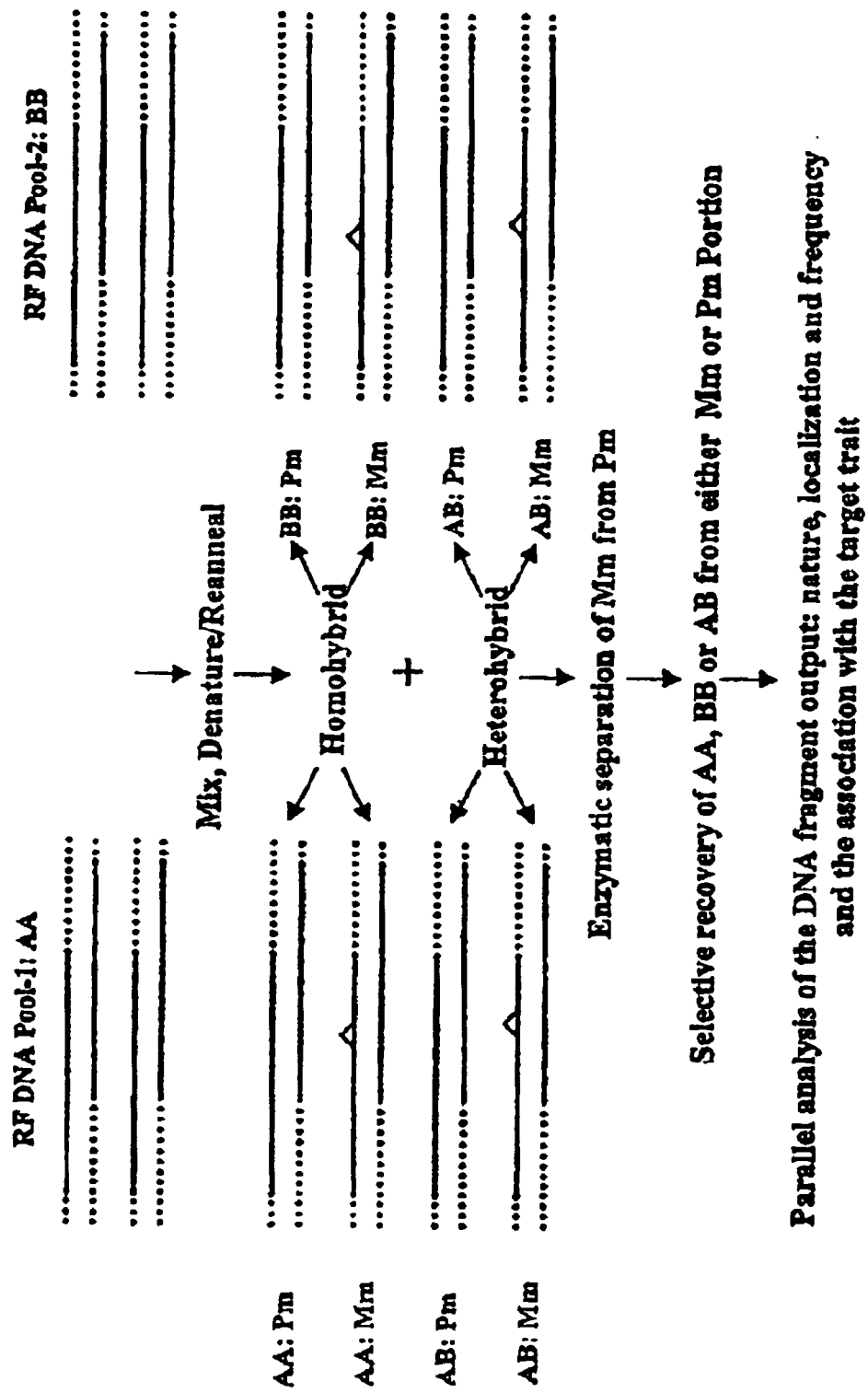
FIG. 8 illustrates general outline of the procedures of the invention. PM: perfectly matched DNA duplex. MM: mismatched duplex with at least one single nucleotide variation. Homohybrid: a DNA duplex in which two strands come from the same source pool, such as AA or BB. It can be either a PM or an MM. Heterohybrid: a DNA duplex in which two strands come from different sources, such as AB. It can be either a PM or an MM. The adapters are not drawn in detail.

FIG. 7 demonstrates another approach to separating homohybrids and heterohybrids. Adapters with one chemical adduct (for example digoxin) are ligated to one DNA pool and adapters with a different adduct (for example, biotin) are ligated to the other pool. Only heterohybrids will contain both adducts allowing them to be differentiated from homohybrids by well-known separation techniques such as use of beads or columns.

Seven strategies based on the modification of LSA adaptor, Smart adapter or regular adapter are provided for selective recovery/amplification of AA, BB or AB (either one of the homohybrid or heterohybrid) from one pot. They are independent but they can be combined with each other or with other designs. The fragment pools recovered/enriched in this way are suitable to be taken as probes for further analysis such as applying into microarrays, FISH, and other SNP typing or gene mapping techniques. The recovered heteroduplex is also applicable to direct sequencing.

Because two primers are required for the recovery of the heteroduplex while only one primer corresponding to the original restriction fragment pool is required for the recovery of one source of homohybrid, the heterohybrid will not be recovered when one source of homohybrid is recovered. But when heterohybrid is desired, 2 primers are employed and the homohybrid adapters will not be amplified. The resultant constructs have no single stranded regions that may disturb the activities of an enzyme such as glycosylase.

The methods of the invention can also be used to estimate the extent of heterohybrid enrichment resulting from mixing, denaturing, and reannealing two or more DNA pools. In this method all the homohybrids and heterohybrids of two samples are amplified and are compared to all the heterohybrids of the two samples. Comparing may be performed by gel electrophoresis, spectrophotometry, or flourometry.

The goal of this invention is to enrich DNA sequences that are related to a disease or any other phenotype of interest. Methods and compositions are described for identifying, isolating and determining the genomic or cDNA positions where the sequences of two DNA samples or pools of DNA samples differ in the relative abundance of each of the four DNA bases. In most applications the two samples to be compared will be generally similar in sequence with variations occurring at less than one position per hundred residues. Methods include designs that make it possible to recover and further analyze DNA duplexes containing single or multiple sites of mismatched bases. Novel procedures introduced here include the enrichment for intact DNA fragments that contained mismatches or that contained perfect matches in such a way that the perfect match or mismatch containing duplexes can be amplified for subsequent analysis; the use of a special class of enzymes, the DNA glycosidases or the like for this purpose; the design of adaptors that permit selective amplification of either heterohybrids or homohybrids from a mixture of reannealed DNA fragments together with the ability to sequence each fragments using a common sequencing primer. In an alternative application, DNA heterohybrids that do not contain mismatches are recovered free of mismatch fragments, and used for mapping regions of identity between the two sources, or within each source.

The pools of DNA fragments, corresponding to mismatch SNP fragments or perfectly matched fragments of heterohybrids or homohybrids, may be divided into subsets by selective PCR amplification, and the fragments identified either by separating them on acrylamide sequencing gels and isolating and sequencing single fragments, or by annealing them to chromosome spreads or to arrays of cDNA or genomic DNA fragments and determining the nature and relative abundance of probe corresponding to homohybrids and to heterohybrids at each position in the array. The fragments in the array may represent cloned fragments of various sizes, such as are present in YAC, BAC, PAC, cosmid, or phage genomic libraries, or phage or plasmid cDNA libraries, or may represent PCR amplified fragments, corresponding, for example, to non-repetitive portions of cDNA or genomic DNA.

DNA samples to be analyzed may be derived from any source, including haploid, diploid, or polyploid genomes, and may include sources from prokaryotes or eukaryotes, including humans as well as model organisms or other mammalian or plant species or microorganisms, or the DNA may be derived from total cDNA, or cDNA libraries prepared form various sources such as different tissues or cell types, or tumors and normal cells of the cell type, including paired samples form the same individual. The DNA samples may be obtained from single individuals or clones of individual organisms, or may be prepared by pooling DNA form multiple individuals, for example from pools of individuals that share a common phenotypic trait or disease tendency. The two DNA sources to be compared will generally but not necessarily always share a large degree of sequence similarity. The two DNA "sources" to be in parallel analyzed can also be two aliquots of one original resource for the convenience to use some special designs to extract the internal mismatch segments of the DNA pool, or to map heterozygosity or homozygosity or Identical-by-Descents. DNA can be pooled form related or unrelated individuals, so that the procedure may be used either for mapping inheritance within families, such as homozygosity mapping, or for mapping allelic associations in unrelated individuals. The DNA sources may be of any complexity. But for highly complex sources DNA fragments may be divided into subsets prior to denaturation and reannealing, so as to obtain more favorable reannealing kinetics. Sometime the subdividing maybe following the denature and reannealing and the separation of perfectly matched DNA from mismatch DNA, for simplified treatment and for favorable resolution of amplification, and so on.

Selective Amplification of Heterohybrids or Either One of the Two Homohybrids Formed in a Single Annealing Reaction.

Figure 9:
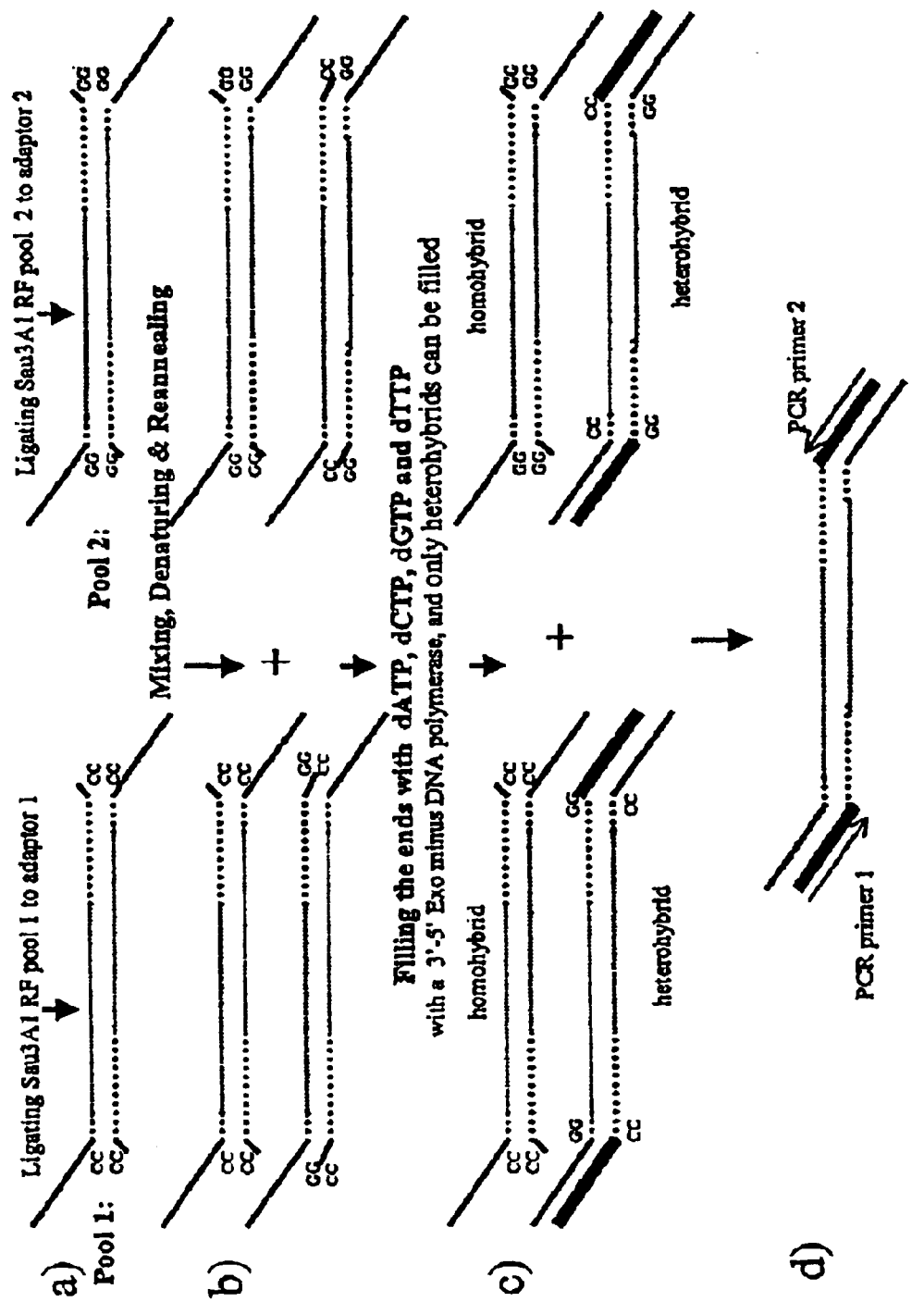
FIG. 9 illustrates basic HeD adapters for recovery of heterohybrids.

The first step of the invention is to selectively amplify the heterohybrids while eliminating the homohybrids by simply employ the HeD adapters. Two pools of DNA, or two subpools of one original pool are separately digested with a frequently cut restriction endonuclease and result 2 restricted fragment (RF) pools. Each pool comprising DNA from a single individual or a mixture from multiple individuals. (FIG. 9, pool 1, and pool 2). RF Pool-1 and RF pool-2 are separately ligated to a pair of HeD adapters that are cohesive to the restricted fragment ends. Like other adapter commonly used, HeD adapters are formed from the annealing of oligonucleotides together and can be ligated onto the ends of other DNA fragments via an appropriate blunt end or recessed 3' or 5' end. The cohesive ends have a necessary requirement that the 5' end must be phosphorylated so both strand both ends can be covalent ligated to the DNA fragment. The other end of the HeD adapters of this invention, which will form the end of the adapter-DNA fragment construct following ligation, contains a region of non-complementary sequence so that the ends will be single stranded of different lengths. In this invention, the 5' terminal sequence of the adapter-DNA fragment construct, is usually longer than the non-complementary 3' terminal section.

In one example, the 3' recessed end HeD adapter ends with the bases CC that forms a mismatch with the corresponding CC in the other strand, which is ligated to RF pool-1. (FIG. 9a). RF Pool-2 DNA is ligated to the other HeD adapter containing a recessed 3' GG end that is mismatched with the corresponding GG in the other strand (FIG. 9a). These two HeD adapters pair together for heterohybrid-directed recovery and amplification, and share the same sequence in the adapter stem and the cohesive end ligated to RF pool. The two DNA construct pools are mixed together, denatured and reannealed. Any homohybrid DNA formed will still contain either the CC or GG mismatch (FIG. 9b). The base mismatches prevent the recessed 3' arm from being filled in by a DNA polymerase that lacks a 3'-5' exonuclease proofreading activity such as Taq DNA polymerase, Tth DNA polymerase, eukaryotic DNA polymerase α, and 3'-5' exo-minus Klenow DNA polymerase. (FIG. 9c). For any heterohybrid formed, the recessed 3' arm will now be correctly base paired with the complementary strand (forming either CC base paired with GG, or GG base paired with CC). The heterohybrid recessed 3' ends can be filled in by the 3'-5' exo-minus DNA polymerase and the four dNTPs (FIG. 9c bold lines). The method is not restricted to the 3' CC ends in this example, but can be carried out with any combination of bases that form a recessed 3' adapter end that is mismatched in homohybrids, and perfectly matched in heterohybrids. There are numerous ways to selectively amplify the heterohybrids once their recessed ends are filled in. For example, PCR primers can be designed that are only functional if the ends are filled in (FIG. 9d, primer 1 and 2). Therefore, only heterohybrids will be amplified while homohybrids will not anneal to the PCR primers.

In each of the examples shown below, referred as Triple-Recovery Strategy (TRS, FIGS. 10–17), the goal is to be able to selectively separate 3 fractions that are formed in a single annealing reaction (referred to as a "single pot"). The 3 fractions are referred to as M, BB, and AB which represent the homohybrid obtained from one DNA pool, the homohybrid obtained from the second DNA pool, and the heterohybrids respectively. The TRS allows a selective recovery of AA, BB or AB from one pot, which significantly reduces the treatment variation to its minimum and benefit the parallel comparison and analysis in the final step. One the other hand, the homohybrids (AA, or BB) can also be separately recovered/amplified from an independent DNA pool of denaturing and reannealing of either one original RF DNA pool alone.

Figure 10:
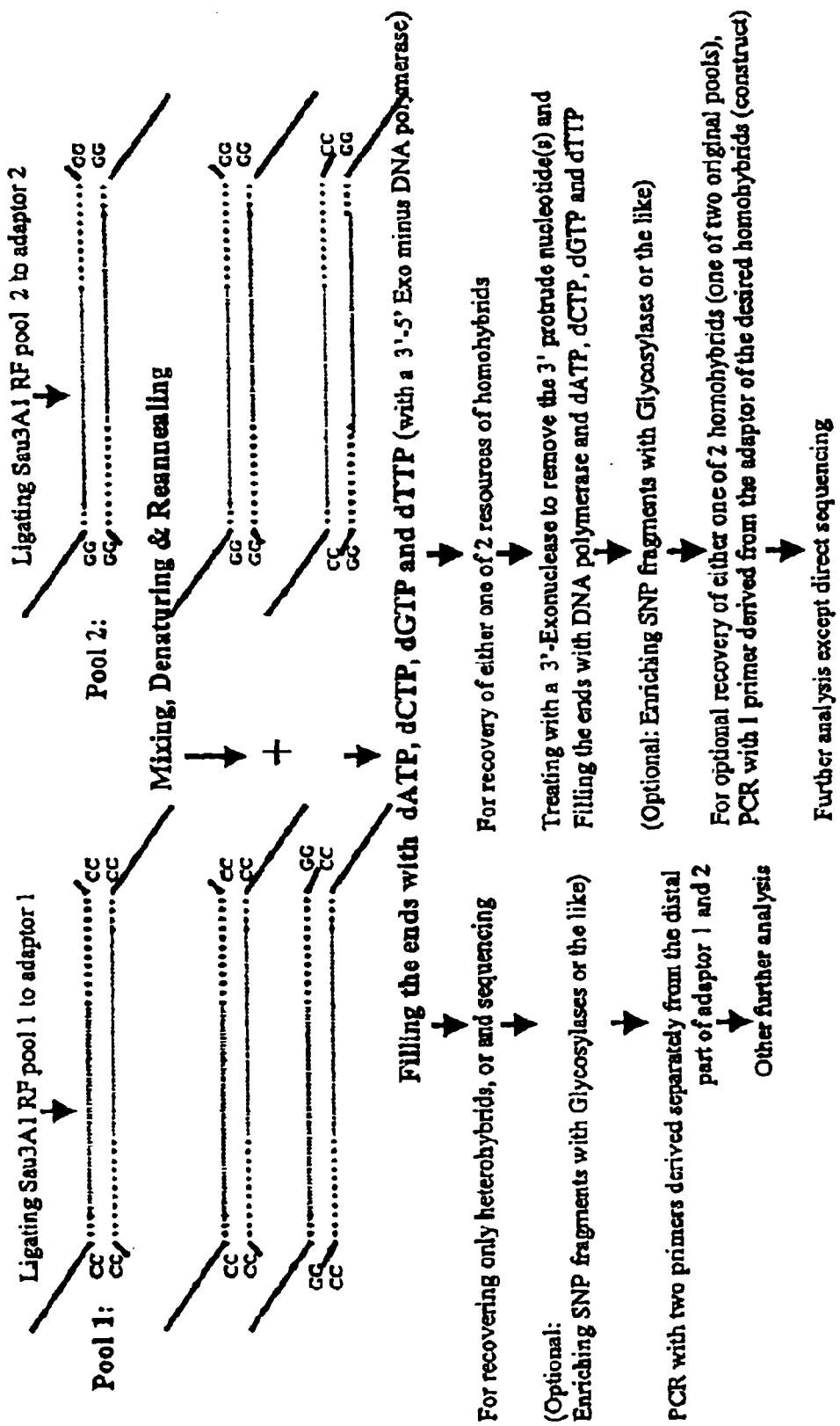
FIG. 10 illustrates schemetically isolating particular DNA duplexes employing a 3' Exonuclease with the HeD adaptor. The 3' Exonuclease can be E. coli Exonuclease I or any proof-reading polymerase such as Klenow fragment polymerase I, pfU polymerase, which usually have both functions of removing the 3' protruding nucleotide(s) and extension.

Beside the recovery of the heterohybrids so said above, an alternative strategy to shown in FIG. 10 allows recovery either one of the two homohybrids instead of heterohybrids is to fill in the ends with a DNA polymerase that possesses a 3'-5' exonuclease proofreading activity (TRS-1, FIG. 10). This will allow the mismatched 3' ends of the homohybrids to be repaired and filled in. Suitable polymerases include Vent DNA polymerase, Pfu DNA polymerase, Klenow fragment of DNA polymerase I, *E. coli* polymerase 1, and T4 DNA polymerase. The target homohybrids can be selectively recovered by the primer (one primer alone) sharing the original free 5' terminal sequence of the adapter of the desired pool from the same one pot of DNA mixture, ex. using primer-1 sharing the original free 5' terminal sequence of the first HeD adapter ligated to RF pool-1 to recover the homohybrids originally from pool-1, and using primer-2 to recover the homohybrids from pool-2. On the other hand, the heterohybrids of the same mixture can be recovered from a aliquot of the same mixture before the treatment of 3'-5' exonuclease activity, as discussed above; in this case no homohybrid will be recovered.

Figure 11:
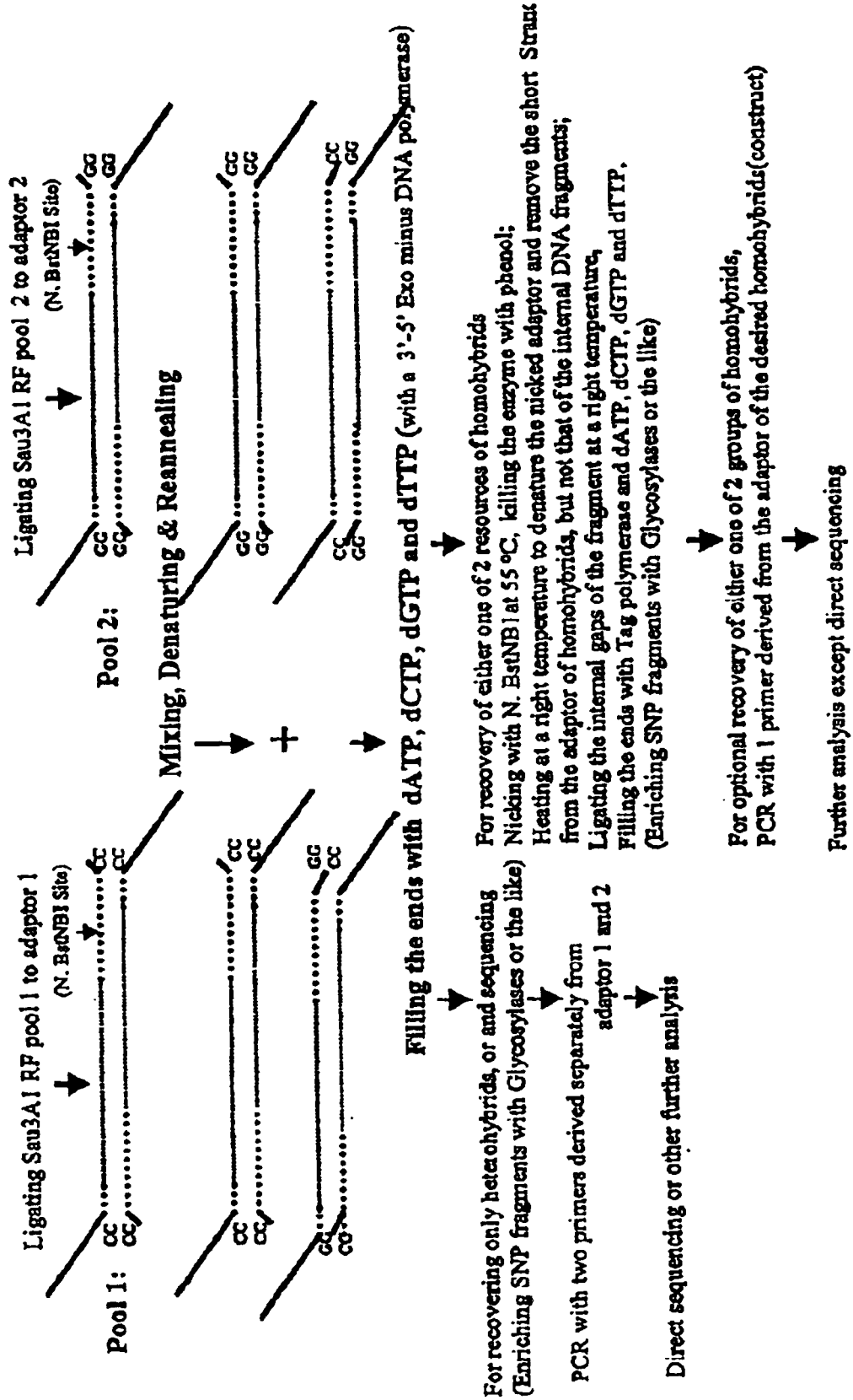
FIG. 11 illustrates schematically isolating particular DNA duplexes employing an N. BstNB1 site in HeD adapters. Blocking the N.BstNB1 sites in the fragments by N.BstNB1 methylase before ligating an adaptor to a fragment pool and the later step of ligating the nicking of the N.BstNB1 in the fragment can be omitted. N.BstNB1 may be substituted by any other enzymes with similar function.
Figure 12:
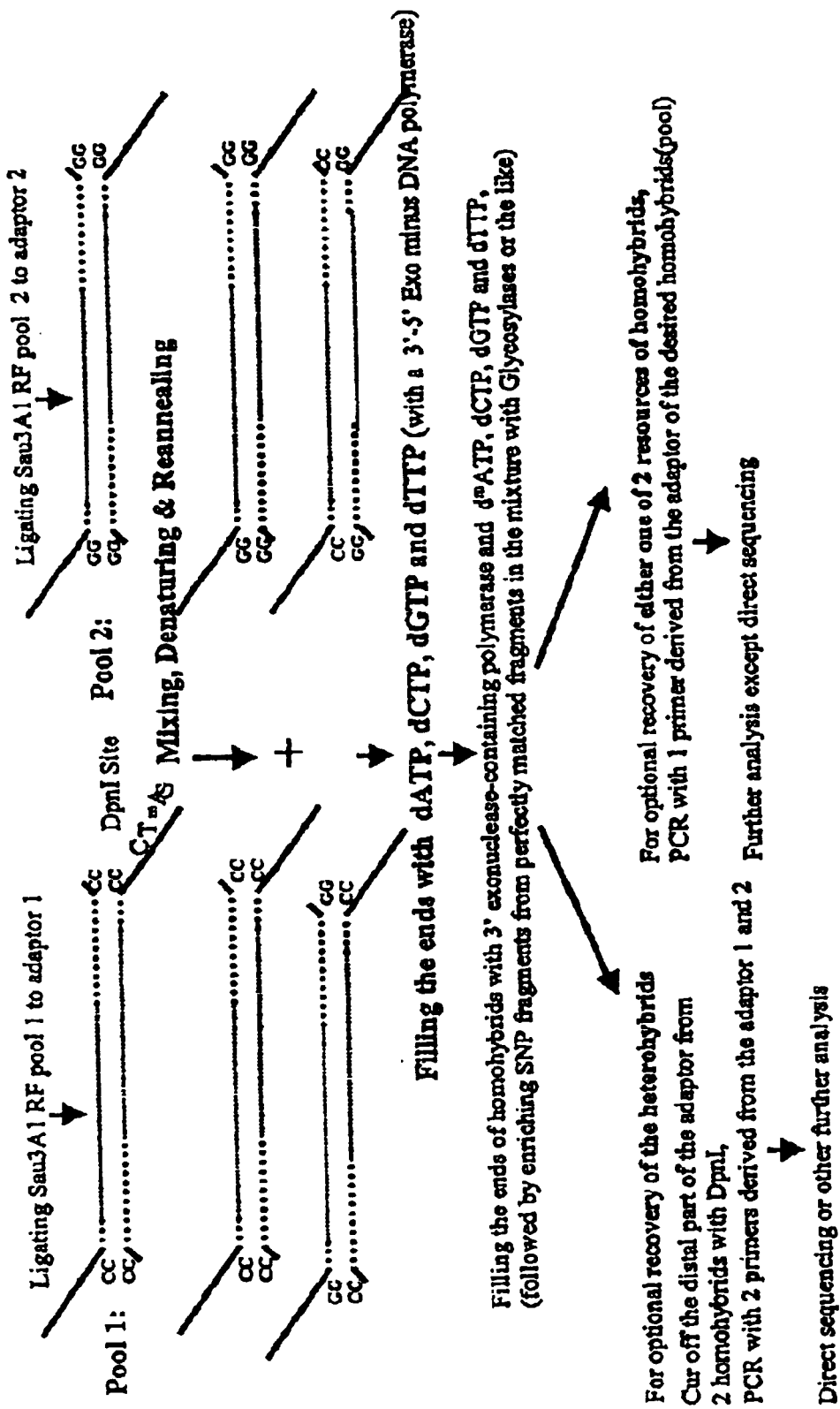
FIG. 12 illustrates schematically isolating particular DNA duplexes employing a 3'-exonuclease with DpnI site in the HeD adapter. In this design, more common treatments are shared among the 2 homohybrids and heterohybrids in one pot, which reduces the variances between the recovery of homohybrids and heterohybrid. Other restriction enzymes similar to DpnI in term of their sensitive/resistance to methylated nucleotide may be used instead of DpnI.
Figure 13:
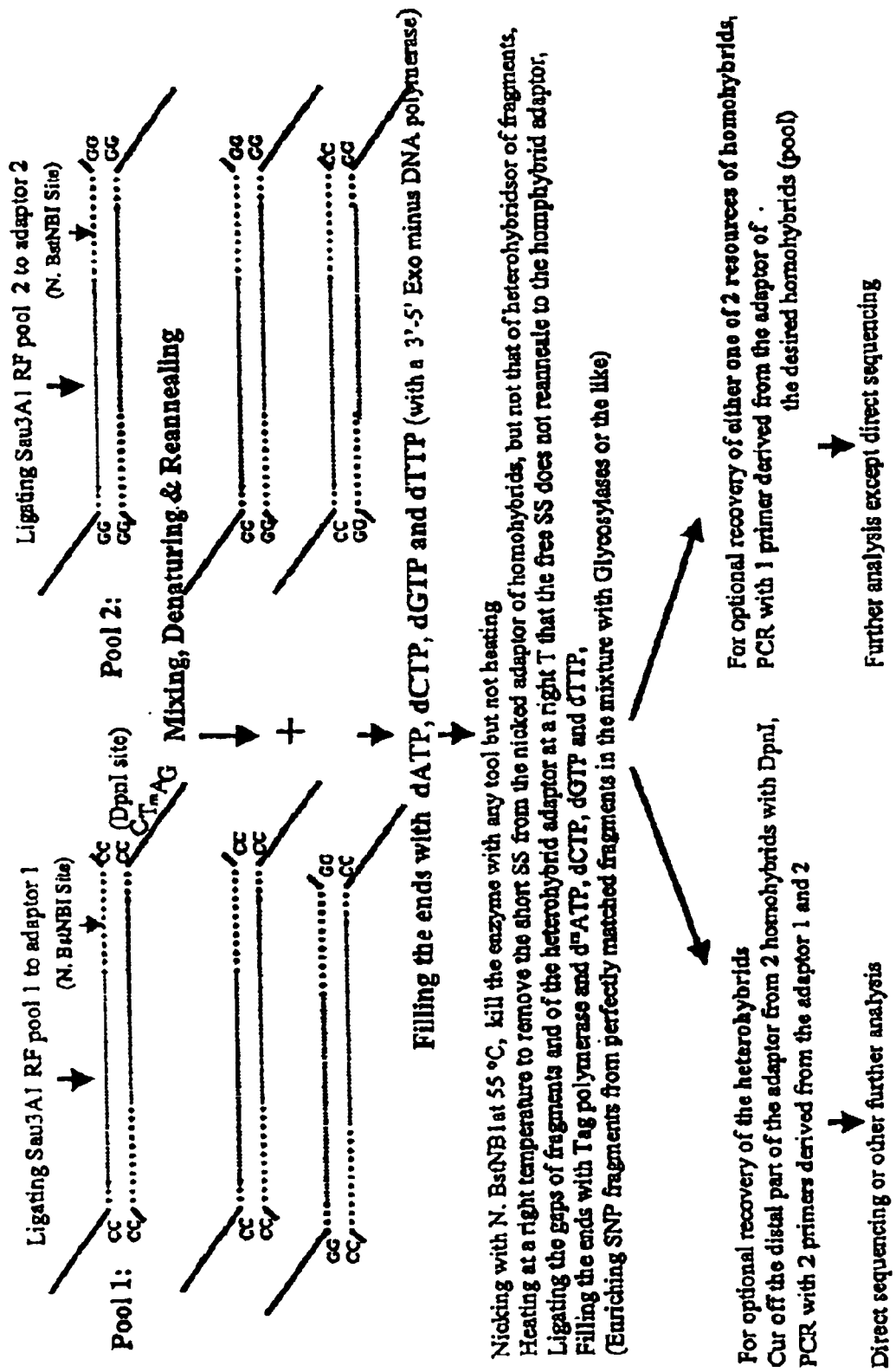
FIG. 13 illustrates schematically isolating particular DNA duplexes employing N.BstNB1 and DpnI site in HeD adapters. This is a kind of combination of strategy No. 2 and No.3.

An alternative way to distinguish heterohybrids from homohybrids is to use a restriction endonuclease capable of nicking only one strand of the DNA such as N. BstNBI (TRS-2, FIG. 11). The first step is the same as in FIG. 9. The 3' recessed end of the heterohybrids are filled in by a DNA polymerase lacking proofreading activity, which can be optionally recovered by PCR with primer-1 plus primer-2. The heterohybrids can also be recovered together with the recovery of homohybrids after all treatment so as to reduce the variation resulted from different to its minimum (see below). The homohybrids cannot be filled in due to the mismatched 3' recessed ends and will not be recovered. However, in this example, the ends are then cut with the restriction endonuclease generating a nick as indicated. It will be possible to heat the DNA to a temperature that causes the 3' ends of the homohybrids to dissociate. Because the 3' ends of the heterohybrids have been extended in the fill in reaction, they may remain annealed at an appropriate temperature. The temperature can be at any level that allows the dissociation of the unextended 3' ends but not the extended ends. Treatment of the DNA with a ligase will close every possible nick in every internal fragment. The homohybrids can be amplified by carrying out PCR with only primer-1 to obtain one homohybrid, or only primer-2 to obtain the other possible homohybrid (FIG. 11). When the distal parts of the adapters of all the homohybrids in another aliquot of the mixture are cut off with DpnI, the heterohybrids can be selectively recovered and amplified from the with primer-1 and 2 via PCR.

When an appropriate restriction endonuclease site such as DpnI is located on the adapter but without N. BstNBI like site or enzyme, following the same treatment of FIGS. 10a–c, the ends of the homohybrids is then filled with methylated dATP and 3'-5' exonuclease-containing DNA polymerase. In this case, one primer can specifically and selectively amplify the corresponding homohybrids. The key point is that this design allows the specific digestion of homohybrids by DpnI and subsequent amplification from the remaining heterohybrids with primer-1 plus primer-2. (TRS-3, FIG. 12). Any restriction endonuclease sensitive to methylation on both strands can be used to replace DpnI.

Another method uses adapters containing the recognition sequence for restriction endonucleases such as DpnI that require methylated bases, plus N. BstNBI for nicking single strand and filling homohybrids instead of 3'-5' exonuclease-containing DNA polymerase. (TRS-4, FIG. 13). The first steps are identical to FIGS. 10a–c with normal dNTPs being used to fill in the HeD adapters in a first 3' end extension reaction. N. BstNBI, or a similar enzyme that nicks a single strand, is then used to remove the mismatched 3' end of the adapter as in FIG. 11. With the mismatched 3' end now removed, a DNA polymerase can be used in a second extension reaction this time using methylated dATP. Homohybrids can be amplified with one corresponding primer alone. Then, both homohybrids can be cut by Dpn1 which recognized the methylated A containing GATC site. Heterohybrids will not be cut and can therefore be selectively amplified by primer-1 plus primer-2. This strategi is a combination of TRS-2 and TRS-3.

Figure 14:
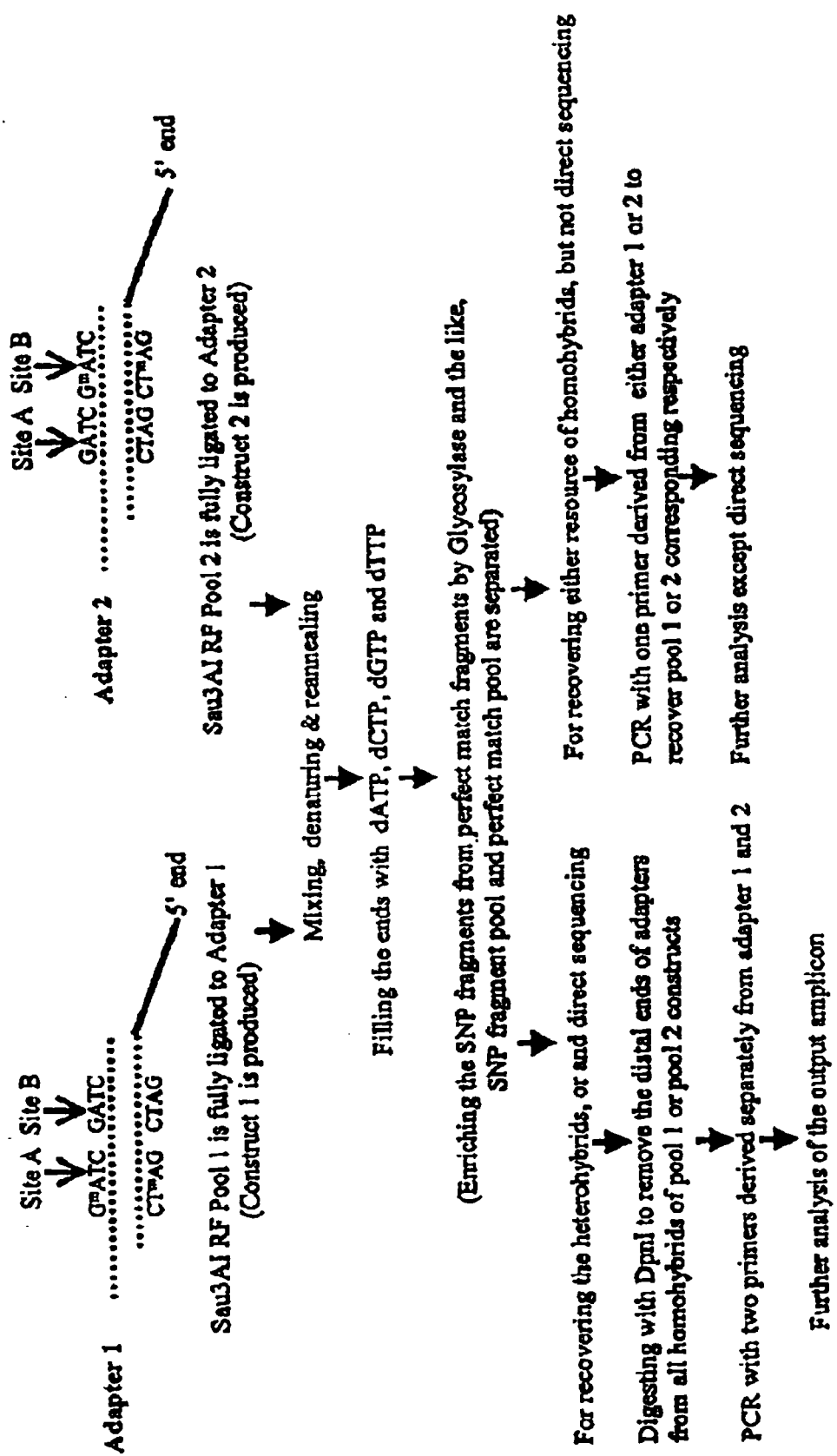
FIG. 14 illustrates schematically isolating particular DNA duplexes employing 2 selectively methylated DpnI sites of adapters. This modified HeD adapter has no free 3' end at two terminals of the constructs. DpnI cuts off Site A of construct 1 homohybrid, and Site B of construct 2 homohybrid, but it does not cut heterohybrid, which is composed of 1 strand from construct 1 and 1 strand from construct 2 and so it is hemimethylated. Because the pool is Sau3AI cut, no protection is required. Other REs that cut their recognition sites only when both strands of the sites are methylated may replace DpnI. Many kinds of adaptors such as regular duplex adaptors or HeD adaptors may be used in this strategy, but they may not be able to separate only one class of the homohybrids of one original-pool from the mixture, nor direct sequencing.
Figure 15:
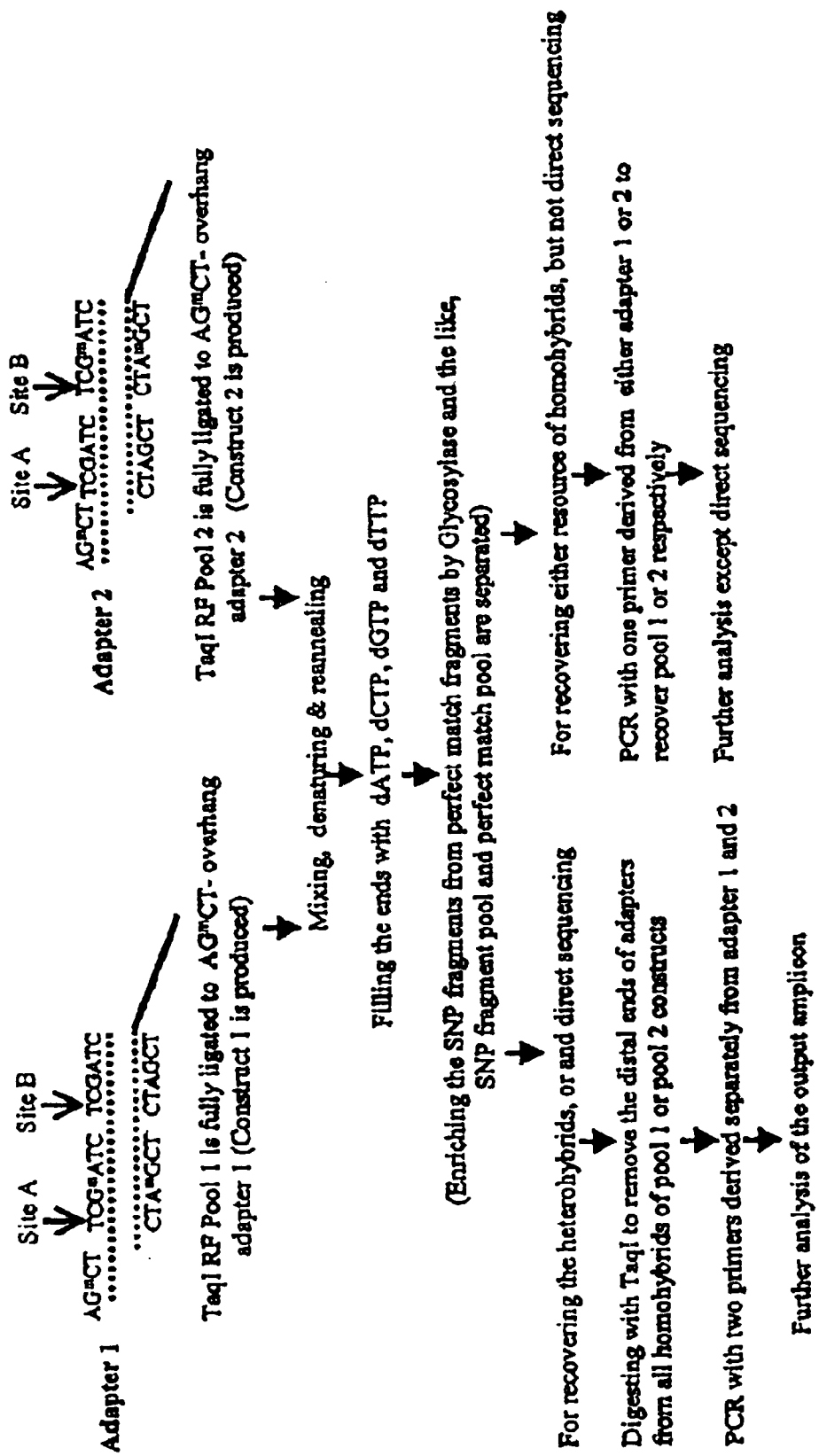
FIG. 15 illustrates schematically isolating particular DNA duplexes employing 2 selectively methylated TaqI sites of adapters. TaqI cuts off Site B of construct 1 homohybrid, and Site A of construct 2 homohybrid, but it does not cut heterohybrid, which is composed of 1 strand from construct 1 and 1 strand from construct 2, and both Sites A and B are hemi-methylated. When the RE pools are prepared by Sau3AI or other REs, they should be treated by TaqI methylase before they are ligated to the adapters. Other REs such as AluI may replace TaqI. Many kinds of adaptors such as regular duplex adaptors or HeD adaptors may be used in this strategy; however, only HeD adapters can be used for direct sequencing the heterohybrids, or selective separating only one class of the homohybrids of one target original pool from the mixture. The modified HeD adapters have no free 3' end and at two terminals of the constructs.
Figure 16:
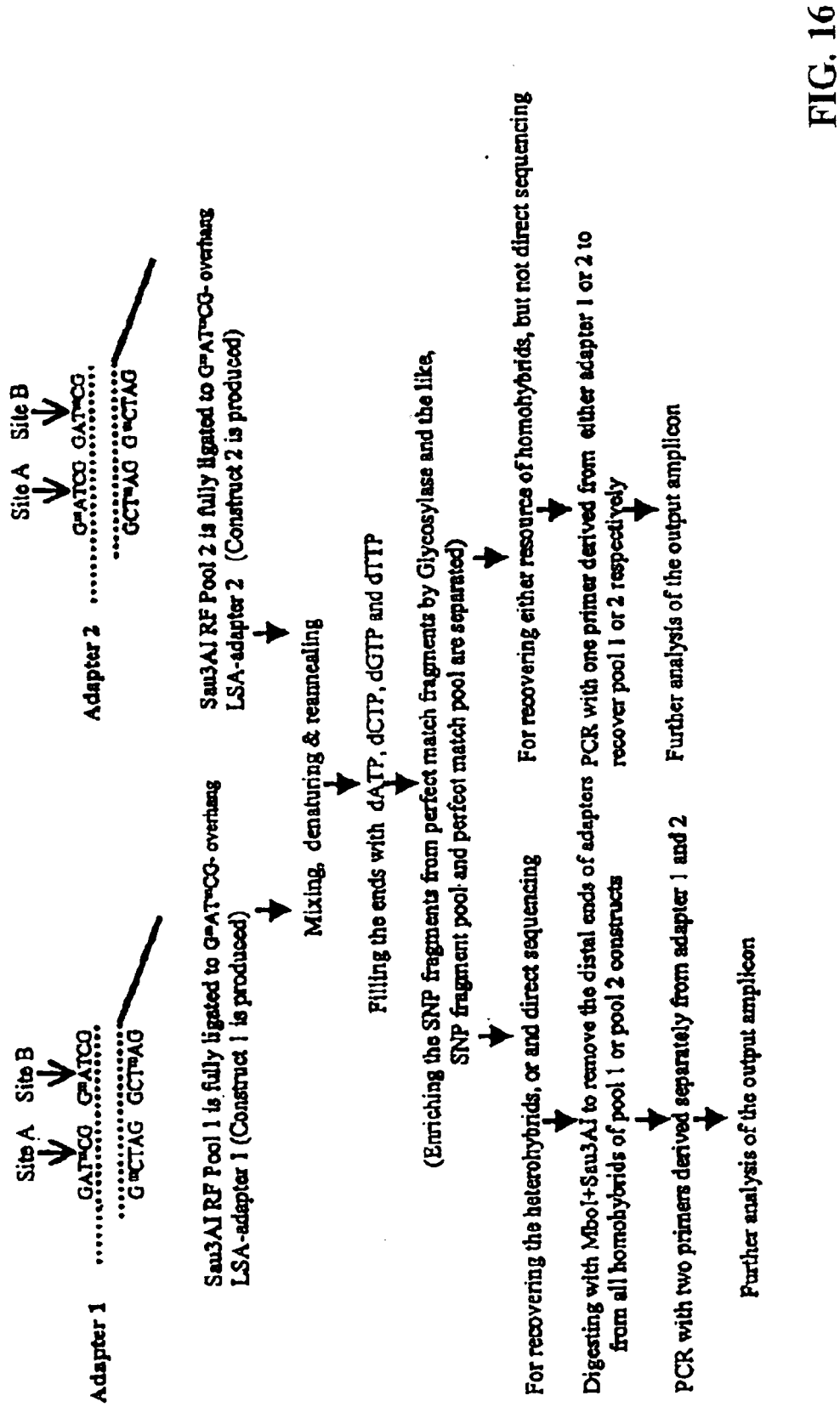
FIG. 16 illustrates schematically isolating particular DNA duplexes employing 2 differentially methylated MboI/Sau3AI sites of adapters. MboI cuts off Site A of construct 1 homohybrid: Sau3AI cuts off Site B of construct 2 homohybrid. Heterohybrids are not cut by any of the two restriction enzymes (REs). G$^m$AT$^m$CG-overhang adapter is used to prevent the ligation site from being cut by either of the two REs. Other RE pairs with similar features of MboI-Sau3AI may be used to replace MboI+Sau3AI. Many kinds of adaptors such as regular duplex adaptors or HeD adaptors may be used in this strategy, but only HeD adapter can be used for direct sequencing, of the heterohybrids, or selectively separating only one class of the homohybrids of one target original pool from the mixture. The modified HeD adapters have no free 3' end at two terminals of the constructs.

FIG. 14 shows another strategy (TRS-5) by employment of a pair of modified HeD adaptors; each adaptor has two differentially methylated DpnI sites After denaturing and reannealing, only homohybrids will be digested by DpnI, but Heterohybrids will not be digested. FIGS. 15 and 16 (TRS-6, and TRS-7) show alternative strategies to obtain either homohybrids or heterohybrids from the same annealing reaction. In these examples, heterohybrids can be selectively amplified using both PCR primers and it can be used directly in DNA sequencing reactions. To recover either one of the two possible homohybrids, the single PCR primer is used that corresponds to the adapter ligated to the DNA RF pool. Here, a pair of regular full double strand adapters work well for these design, but only HeD adapters/derivations are suitable for direct sequencing the heterohybrids, and only HeD adapters/derivations are suitable for selective recovery of either one of the two homohybrids from the mixture. In contrast to it, regular full duplex adapters are neither suitable for direct sequencing, nor separating one class of homohybrids from another class of homohybrids. Again, these strategies will work well for many other restriction endonuclease that recognizes methylated bases.

Figure 17:
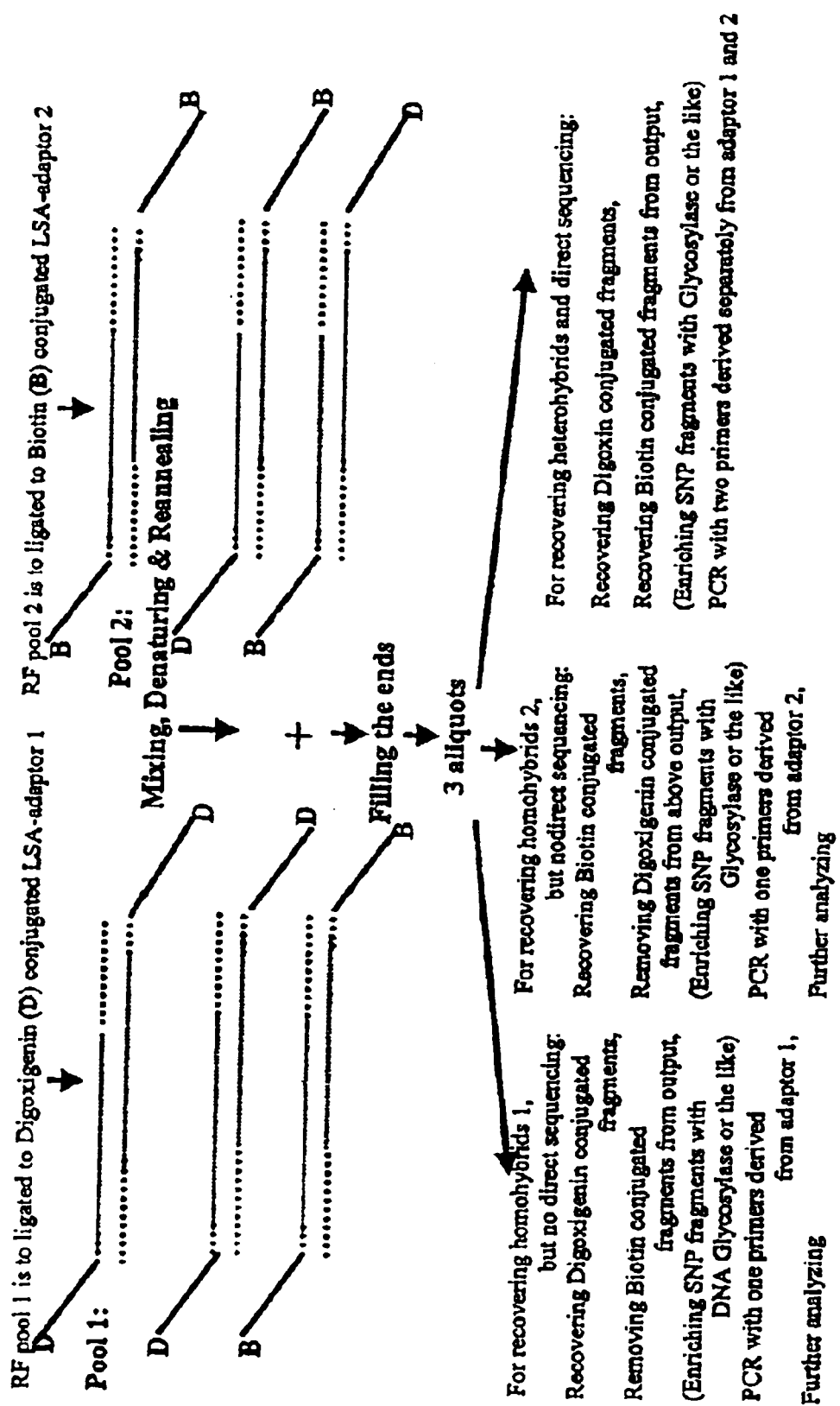
FIG. 17 illustrates schematically isolating particular DNA duplexes by physical-chemical moiety. The modified HeD adapters have no free 3' end at two terminals of the constructs. A duplex adaptor can be used to replace an HeD adapter, but only HeD adapters can be used for direct sequencing of the heterohybrids, or separate recovery of either one of two classes of homohybrids. Any two capture moieties can be used to replace biotin and digoxin.

TRS-8 demonstrates another approach of chemical/physical separating homohybrids and heterohybrids (FIG. 17). Adapters with one chemical adduct (for example digoxin) are ligated to one DNA pool and adapters with a different adduct (for example, biotin) are ligated to the other pool. Only heterohybrids will contain both adducts allowing them to be differentiated from homohybrids by well known separation techniques such as use of beads or columns. Also, a pair of standard double strand adapters work well for these design, but only HeD adapters is suitable for direct sequencing the heterohybrids, and selective and separate recovery either one of the two homohybrids.

Figure 18:
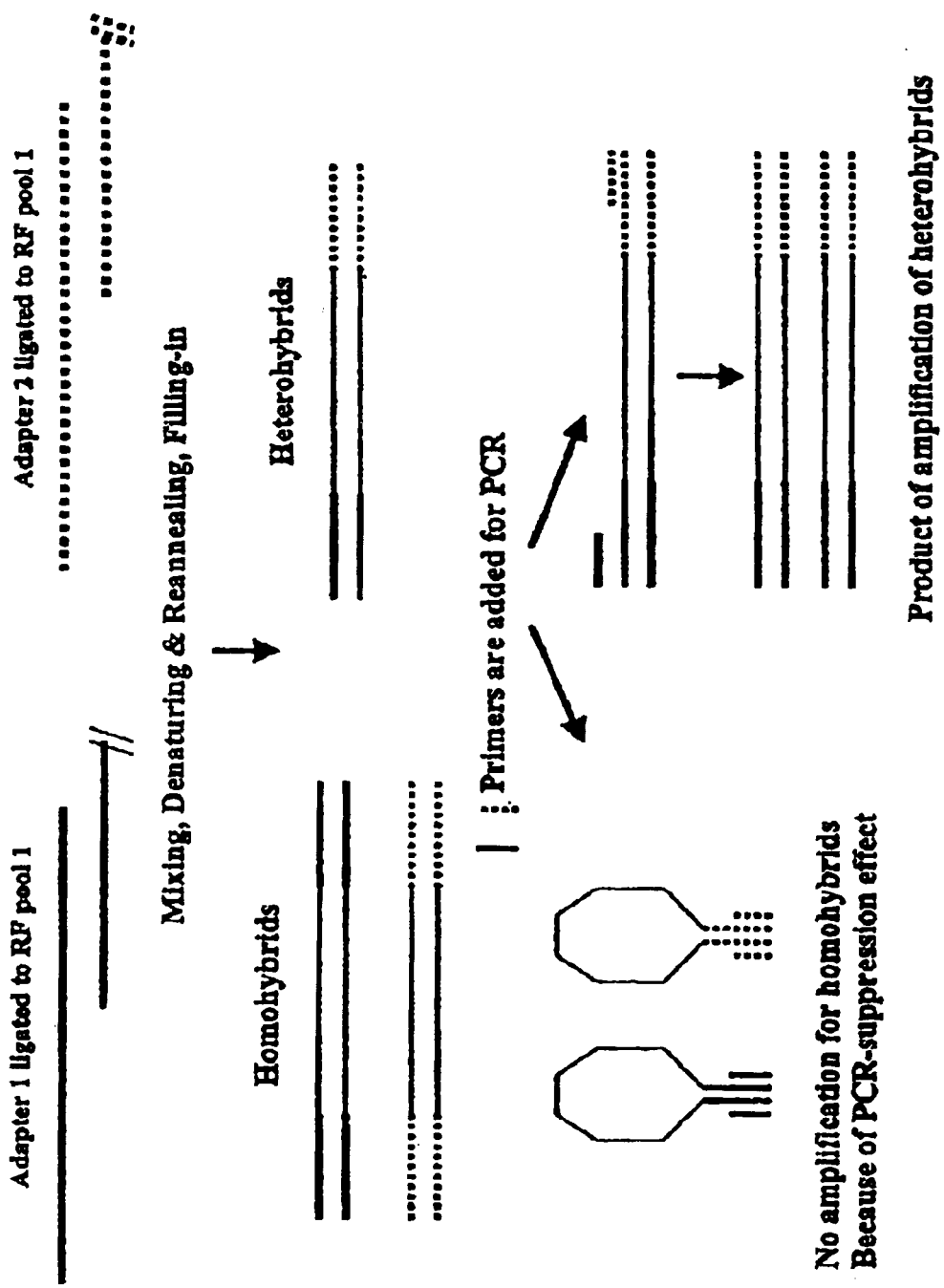
FIG. 18 illustrates schematic for alternative HeD adapters. Nine strategies based on the modification of HeD adapter/derivation are provided for, selective recovery/amplification of AA, BB or AB (either one source of homohybrids, or heterohybrids) from one pot of DNA mixture. Actually, HeD adaptors/derivations ligation plus denature, reannealing and filing steps alone, without any modification of the adaptor, can be applied to specifically recover/amplify AB from the mixture. The modifications are given from additional recovery of AA or BB as well as AB from one pot of DNA mixture from two sources of DNA hybrids treated by denature, reannealing and end-filling, which benefits the parallel comparison, or subtraction of the neutral variation within one pool (usually, the control pool) from the genetic difference between 2 pools, to extract the trait concordant genetic markers. The different strategies given here are independent but they can be combined with each, other or with other designs.

Alternative strategy for heterohybrid recovery and amplification is based on PCR-suppression effect (Diatchenko L, et al., Proc. Natl. Acad. Sci. USA, 93:6025–6030, 1996; Matz M, et al, Nucl. Acids Res., 27: 6–8, 1999) and the alternative HeD adapter. The principles of PCR-suppression effect is that long inverted terminal repeats flanking DNA fragments can selectively suppress the polymerase chain amplification of these DNA fragments when a primer corresponding to the distal half of the repeat are used. We introduced this principle and modified the strategy for our purpose of selective recovery/amplification of the heterohybrids (FIG. 18, TRS-9). A pairs of adapters with different sequences are ligated to a pair of RF pools to be analyzed, or two aliquots of one original RF pools when it is required to extract the internal mismatch segments of the DNA pool, or to map heterozygosity or homozygosity or Identical-by-Descents. Each adapter has a long and a short oligonucleotides, of which the 5' end of the long strand is to the outside of the constructs, and the 5' end of the short oligonucleotides is onto the fragment end and unphosphorylated and so no covalent ligation occur when this adapter is ligated to DNA restriction fragment. The 5' part of the long strand remains to be free single strand and the sequence of this free single strand part is long enough for PCR primer priming, usually longer than 20 bases. After mixing, denaturing, and reannealing the constructs of RF pool1 and RF pool12, melting off the short strand of the adapter and filling the hybrids. When a pair of primers complementary to the two different newly extended 3' ends are used for amplification via PCR or RCA, the heterohybrids are preferentially recovered and amplified, while the amplification of the homohybrids is suppressed because of the long inverted repeats flanking the two ends.

In the step of the recovery or amplification of the target hybrids for the strategies above, rolling cycle amplification (Fire A, et al. Proc. Natl. Acad. Sci. USA, 92:4641–4645, 1991; Lizardi P M, et al. Nat Genet. 19(3):225–32, 1998) may be used to replace PCR, whereby a splint oligonucleotides with two end sequences corresponding two end of the target constructs is used to circulating the target strands.

Several strategies based on the modification HeD adapter or regular adapter are provided for selective recovery/amplification of AA, BB or AB (either one of the homohybrid or heterohybrid) from one pot. They are independent but they can be combined with each other or with other designs.

Use of DNA glycosylases to Select Mismatched DNA.

A novel approach is also described here to use DNA glycosylases to carry out polymorphism analysis and to identify SNPs with heterohybrid or homohybrid DNA.

In the examples above, heterohybrids may be formed from two individuals or two pools of DNA that are themselves formed from the mixture of many individuals' DNA. In the example below, the use of individual patients' DNA and control DNA from an individual is used, however, the same principals apply to pools of DNA. Regions of low polymorphism that two patients share in common will tend to result in perfectly matched double stranded DNA, in a heterohybrid.

To identify SNPs in heterohybrid duplex DNA, the heterohybrids may be contacted with a DNA glycosylase to nick the heterohybrid DNA. DNA glycosylases include thymine glycosylase, E. coli mut Y protein, uracil-DNA glycosylase, MBD4, thymine-DNA glycosylase, 8-oxoguanine glycosylase, or N-methylpurine-DNA glycosylase. The glycosylase nicks the heterohybrid DNA, and the heterohybrid duplexes with nicks are identified as containing a SNP. The molecules containing steps can be separated from molecules not containing SNPs, for example by immobilizing or attaching the DNA glycosylase to a solid support. Solid supports include beads and resins used in chromatography, slides or chips.

Methods for binding a DNA glycosylase to mismatched DNA are also disclosed. DNA is bound to a DNA glycosylase by contacting a DNA sample with EDTA to withdraw $Mg^{+2}$ from the DNA. EDTA may be contacted with the DNA sample and $Mg^{+2}$ removed by techniques such as dialysis. The DNA sample is then contacted with a DNA glycosylase.

DNA that is bound to a DNA glycosylase is also released from the DNA glycosylase by methods of the invention. The DNA bound to the DNA glycosylase may be released by contacting with $Mg^{+2}$.

Regions of polymorphism result in mismatched basepairs that can be distinguished by DNA glycosylases as described below. The procedures can also be repeated for two control individuals not expressing the phenotype of interest. This will produce a sample of control heterohybrid DNA that can be compared to the patient heterohybrids. The procedure can also be carried out to obtain heterohybrids containing one strand of patient DNA hybridized to a strand of control DNA. This will be used to determine polymorphisms between the patient population and the controls.

As we discussed before, both homohybrid and heterohybrid can be either perfect matched duplex or mismatched duplex. Separating and enriching of SNP fragments or PM fragment from a mixture with high enough specificity and sensitivity is a key issue in genetic analysis. This invention declares here that DNA Glycosylase is a useful tool for this purpose.

DNA glycosylase binds mismatched DNA with high specificity in an optimized condition with the cost that some SNP fragments may be together with PM fragment not being bound. Then the bound SNP fragments can be recovered. In this case, the SNP fragment is highly specifically separated from PM fragment and efficiently enriched. Alternatively another condition makes the PM fragment free from binding by DNA Glycosylase in a high specific mode with the cost that this enzyme may bound some PM fragments together with SNP fragments. In this case, the PM fragment is highly specifically separated from SNP fragment and efficiently enriched. The key point is to separate and enrich SNP fragment or PM fragment in separate steps and under different optimized conditions. An immobilized DNA Glycosylase in a fashion of any bead/resin column such as Glutathione-Sepharose agarose, His6 resin or any other solid matrix or free magnetic bead is presented here for specifically separate and enrich SNP fragments from PM fragments. Other fashions may also useful, for example, a recognition and binding reaction in a solution of the DNA Glycosylase with DNA fragments may be used to combine with gel shift, the binding and unbinding portion of DNA fragments can be separated and recovered.

In the procedure to separate mismatch fragments from perfectly matched fragments, the DNA samples are treated with one or more DNA glycosylases, most typically with human or methanobacterial thymidine glycosylase. The treatment is firstly performed ideally in a buffer without magnesium but with EDTA, under which condition the enzyme remains bound to the sugar aldehyde formed when the base is released. The enzyme is used in the form of a fusion protein that may be captured before or after reaction with the DNA. In a typical embodiment the enzyme is used as a fusion protein with glutathione transferase, and the fusion protein is bound to glutathione coated beads before reaction with the DNA. After binding DNA the beads containing the enzyme are washed several times to release non-specifically bound DNA, then DNA containing abasic sites is released by the addition of magnesium. The precise binding and washing conditions vary depending on whether the experiment is designed to maximize the purity of the mismatch containing, or alternatively the perfect match DNA fragments.

In an alternative method, in combining with the free DNA glycosylase recognizing and modifying the mismatched fragment and leaving an abasic (AP) site and an associated aldehyde in one or two of the duplex, a specific chemical in conjunction with a GST, His6, biotin or other groups, which is used to recover the SNP fragments in later steps, is employed here to trap the fragments with AP site(s)/ aldehyde. An example of this kind of chemicals is the hydroxylamine or hydrazide derivative that forms a stable oxime bond with the open-chain aldehydes generated upon AP site formation, such as (but not limited to) FARP [5-(((2-(carbohydrazino)-methyl) thio) acetyl)-aminofluorescin, aminooxyacetyl hydrazid] (ref: Makrigiorgos G M. Int J Radiat Biol. 1998;74(1):99–109, Maulik G. Nucleic Acids Res. 1999; 1;27(5):1316–22). Before applying this procedures, the RE fragment pool is required to be treated with hydroxylamine to remove the possible spontaneously produced aldehydes.

Parallel Analysis of the Output Fragment Pools

In order to obtain the SNP information as well as IBD information in terms of their nature, frequency, localization and finally the genetic and possible physical mapping of the target trait, different output fragment pools are necessary to be analyzed in a comprehensive or parallel fashion. The possible analysis techniques include microarray hybridization, gel display, subtractive hybridization, FISH (fluorescent in situ hybridization), or other techniques. Two or more of the four output fragment pools, i.e., the PM homohybrids from the control pool, the SNP homohybrids from the control pool, the PM heterohybrids, and the SNP heterohybrids, may be analyzed parallel in one procedure/ test.

Different methods can be used to identify the genomic origin or sequence of fragments that do or do not contain sequence variants in each pool, or between the two pools, depending on the research requirements. If only a small number of differences are expected, for example, in comparing tumor and normal tissue, or an inbred strain of mousse and its mutated offspring, then representational difference analysis (RDA) or another nucleic acid subtractive method may be used to subtract from the heterohybrid mismatch fragment pool (SNP heterohybrids) those fragments that are also represented in either homohybrid mismatch pool (SNP homohybrids). In another embodiment, in searching for fragments that are identical by descent (IBD) or for homozygosity mapping, the perfect match fragment pool (PM fragments) from a phenotypically marked group may be subtracted with driver from the mismatch fragment pool (SNP) gomohydrids of the control DNA.

In another embodiment, the amplified fragments from the mismatch preparations within pool 1, those within pool 2, and those within the heterohybrid mismatch pool may be compared and searched for differences in various ways. This can be done by amplifying the fragments with radioactive primers and running fragments form the various pools on display gels in parallel, followed by autoradiography or phosphoimager analysis. Alternatively the fragments from each pool or from any pair of pools may be differentially labeled, either with radioisotopes with distinguishable emissions, or with fluors that emit light at different wavelengths. The labeled fragments may be annealed to arrayed cDNA pools, arrayed genomic fragments, or chromosome spreads, etc. and the presence and relative intensity of signal from each pool at each position on the arty quantitatively recorded.

For example, SNP heterohybrids between the DNA pool of the trait population and its control can be labeled as one color (ex. red) of probes, the SNP homohybrids within its control pool or the PM heterohybrids can be labeled as the different color (ex. green) of probes. These two complementary probe pools are hybridized to a set of DNA arrays, then the trait associated SNPs will show their nature, localization as well as the frequency information.

This invention differs from GMS approach in many aspects. First, It screens all possible potential related SNPs of the entire DNA pool analyzed, which is supposed to be the best genetic mapping marker; if desired, it also combining uses identical sequences (IBDs, or sometimes IBSs if desired) for dual-signals mapping of the same trait, which makes it more powerful. In GMS, IBDs are the only information it may extract out for the mapping analysis. The information for the regions of heterozygosity in the given genome may be able to extract for a given individual by GMS (U.S. Pat. No. 5,376,526), but most of the real SNP information is actually unavailable because GMS uses MutHLS system to recover the PM fragment. And the MutHLS system requires a GATC site for its activity, and only long enough DNA segment (2–20 kb) may contain this site and so the non-IBD fragment almost always contains one or more SNP site that makes SNP information unavailable. Second, a DNA pool from many individuals (pooling strategy), besides a DNA pool from an individual, can be used for one procedure analysis in the invention presented here, because GMS uses the DNA from only one individual as a DNA pool but not any of the pooling strategy. Third, either one DNA pool alone or a trait DNA pool combining with its control pool can be the right starting materials for this invention. On the other hand, GMS uses two related individuals, ex. an affected-relative-pair, or two other genomic that is supposed to contain IBD sequences, and extracts the IBD information between them, so no control information is obtained. Four, cDNA, or genomic DNA or a collection of a number of genes can be used for the analysis of this invention. In GMS, only genomic DNA can be the right sample because it is target on genomic IBD sequences. Five, a simple design of HeD adapters is designed in this invention to recovery heterohybrids, and its derivations as Triple-Recovery-Strategy (TRS) can be used to recovery either one of the homohybrids besides the heterohybrids from one pot of mixture for a parallel analysis. GMS uses a combination of a restriction methylase and methylation-sensitive endonuclease to recover the heterohybrids, which is more complex and laborious and also the homohybrids is unable to be recovered from the same pot. Six, DNA glycosylase is much more specific and sensitive than MutHLS in term of the recognition discrimination between PM and SNP fragments in vitro. Seven, an immobilized enzyme approach is designed for a convenient and efficient recover the desired fragment pools outflow.

This invention differs from the current gene cloning strategies, such as functional cloning and positional cloning, or candidate gene approach, in that it does not require any prior information of the disease or trait related protein, nor the position of the gene. It directly and greatly amplifies/ captures any strong or weak association/linkage of the SNPs throughout whole genome or cDNA pool.

It is also differs from the other SNPs screening or typing approaches available currently, in that this approach simultaneously screens every and any SNPs from the entire genomic DNA/cDNA pool/subpool without any prior information. It highly specifically captures/enriches the SNP-containing fragments related to a traits for further analysis such as allele nature as well as quantitative frequency analysis, while excluding the unrelated or neutral SNPs or taking them aside as the controls for further analysis.

Again, this approach can, in the same one procedure, distinguish the SNPs within one pool from the SNPs between 2 pools, so that it greatly reduces the background of the gene mapping, and makes the results easy to interpret. In addition, this invention also provides an improved IBD screening technique, and a method for selectively amplifying a given DNA resource from a mixture DNA pool.

This invention provides a highly efficient mapping approach for any complex trait disease as well as simple Mendelian diseases or somatic mutation or drug response variation, in an outbreed as well as an inbreed population. It can be used as a highly efficient approach for screening/discovery of the SNPs in a entire, or a part of, complex genome/cDNA pool, enabling a rapid establishment of a complete SNP genetic map of the whole genome/cDNA pools and fast and efficiently evaluating the candidate genes. It can also be used for highly efficient profiling/sorting of the DNA/cDNA SNPs of any sample pair such as a chemically, physically or biologically treated sample and its untreated control.

This approach has the advantages of high sensitivity, high specificity, high-throughput, high efficiency, and high-compatibility with other related techniques.

Experiment 1

Test to separate mismatched from matched DNA duplexes. A perfectly matched duplex formed with synthetic 60 nt oligonucleotides (PM1 annealed to PM2) and a 76 bp duplex containing a G/T mismatch (MM1 annealed to MM2) were mixed together as the starting template mixture. These were labeled on the 5' end with $^{32}P$ using PNK obtained from New England Biolabs using the manufacturers suggested protocol. These were loaded onto a 0.1 ml column of immobilized hTDG or mTDG. With the steps of binding, washing and eluting, the 76 bp and 60 bp fragments were separated at different optimized conditions: the perfectly matched fragment passed through the column and were further specifically washed off (4 steps of washing). The mismatch fragment was retained in the column, and then eluted with two 1 ml washes. Fractions from different steps were collected, purified, and loaded onto an 8% sequencing gel. The concentration of matched or mismatched duplex in each fraction was determined by the level of $^{32}P$ radioactivity determined with a phosphoimager. The PM duplex and Mismatched duplex was separately enriched by $\geq 500$-fold. That is, PM duplex recovered in the flow through fraction had less than one part in 500 contamination with mismatched duplex, and mismatched duplex recovered in the flow through fraction had less than one part in 500 contamination with PM duplex.

Following the selective removal or enrichment of DNA containing basepair mismatches or having no mismatches, the novel adapters described above can be used to selectively amplify or recover the heterohybrids or either possible homohybrid for further analysis. For example, the output amplicons can be analyzed by differential display, used to make DNA probes, or used in DNA sequencing reactions. The novel adapters can also be employed in many other ways to achieve separation of heterohybrids and homohybrids and are not limited to the use of PCR or physical capture of chemical moieties, such as biotin, rhodamine, or FITC. For example, a person skilled in the art could use the adapters to initiate a rolling circle amplification reaction (Lizardi, P. M., (1998) Nature Genetics, vol 19, 225).

Our method is superior to an earlier method employing MutSLH to eliminate homohybrids and to eliminate mismatched DNA (Nelson S F et al. Nature Genetics, 1993, 4:11–18). The Mut SLH method can only be used for DNA fragments containing the MutSLH recognition sequence (GATC) and requires the extra step of DNA methylation in order for MutSLH to be functional.

Methods

Glycosylases: hTDG (human G/T mismatch-specific Thymine-DNA glycosylase) was cloned in a modified version from the mRNA of human JY lymphoid cell line based on the sequences reported. mTDG (the archaeon *Methanobacterium thermoautotropicum* DNA mismatch N-glycosylase (Mig.Mth)) was cloned in a modified version from the DNA of the archaeon *Methanobacterium thermoautotropicum*. Both were highly expressed in *E. Coli*, purified to homogeneity and also separately immobilized onto Glutathione Sepharose 4B beads (Amersham Pharmacia Biotech AB).

```
Oligonucleotides
PM1(60):
    CCG TGG TAC TTA CAT CGA GAG ATC CG*C TTG GTG TGG ATT
CAC GCA CGT AGA CCG ATT CCT PM2(60)
    AGG AAT CGG TCT ACG TGC GTG AAT CCA CAC CAA GC*G GAT
CTC TCG ATG TAA GTA CCA CGG MM1(76T)
    GATCCGTCGACCTGCACCGTGGTACTTACATCGAGAGAATAGCTTGG
TGTGGAT.TCACGCACGT.AGACCGATTC.CT MM2(76G)
    GATC.AGGAATCGGT.CTACGTGCGT.GAATCCACAC.CGAGCTATTC.T
CTCGATGTA.AGTACCACGG.TGCAGGTCGA.CG
```

Binding Buffer:

Hepes pH7.5, KCl 50 mM, EDTA 5 mM, ZnCl 0.2 mM, DTT 1 mM, BSA 0.25 mg/ml at 37 C. for 2 hours.

Washing Buffer:

Hepes pH7.5, KCl 50 mM, EDTA 5 mM, ZnCl 0.2 mM, DTT 1 mM, BSA 0.25 mg/ml with NaCl in concentrations of 50 mM, 100 mM, 150 mM, and 200 mM at 37 C. for 2 hours.

Elution Buffer1

Hepes pH7.5, KCl 50 mM, $MgCl_2$ 5 mM, ZnCl 0.2 mM, DTT 1 mM, BSA 0.25 mg/ml at 37 C. for 2 hours.

Elution Buffer1

Hepes pH 8.0, Glutathione 15 mM, NaCl 100 mM at 37 C. for 2 hours.

complementary to a 3' terminal sequence of a second DNA strand, wherein the 5' terminal sequence is longer than the 3' terminal sequence, wherein said 5'-terminal

What is claim is:

1. A method to selectively amplify or recover heterohybrid DNA molecules resulting from mixing, denaturating, and reannealing two or more DNA pools, wherein each of the pools comprises DNA from a different individual or a mixture of DNA from multiple individuals comprising:

ligating first Y-shaped adapters onto a first pool of restriction endonuclease digested DNA molecules, wherein the first Y-shaped adapters comprise a complementary and a non-complementary end, said non-complementary end comprising a 5' terminal sequence of a first DNA strand that is non-complementary to a 3' terminal sequence of a second DNA strand, and wherein the 5'-terminal sequence is longer than said 3'-terminal sequence;

ligating second Y-shaped adapters onto a second pool of restriction endonuclease digested DNA molecules, wherein the second Y-shaped adapters comprise a complementary and a non-complementary end, said non-complementary end comprising a 5' terminal sequence of a first DNA strand that is non-complementary to a 3' terminal sequence of the second Y-shaped adapters is longer than said 3'-terminal sequence of the second Y-shaped adapters, and wherein the 3' terminal sequence of the first Y-shaped adapters is complementary to said 5' terminal sequence of the second Y-shaped adapters and the 3' terminal sequence of said second Y-shaped adapters is complementary to said 5' terminal sequence of said first Y-shaped adapters;

mixing, denaturing, and reannealing the first pool ligated to the first adapter with the second pool ligated to the second adapter to form a mixture containing heterohybrids and homohybrids;

extending complementary 3' terminal nucleotides of the heterohybrids using a DNA polymerase that lacks a 3'-5' exonuclease activity to form new 3' ends on the heterohybrids; and amplifying the heterohybrids in the mixture using first and second primers complementary, to the new 3' ends, whereby the heterohybrids are selectively enriched in the mixture containing heterohybrids and homohybrids.

2. The method of claim 1 wherein the step of amplifying is carried out by rolling circle amplification, wherein one, or both of the new 3' ends serve as a primer.

3. The method of claim 1 wherein the step of amplifying is carried out by polymerase chain reaction.

4. The method of claim 1 wherein the non-complementary 5' terminal sequence of the first and second Y-shaped adapters is between 2 and 50 nucleotides and the non-complementary 3' terminal sequence of the first and second Y-shaped adapters is between 1 and 49 nucleotides.

5. The method of claim 1 wherein the complementary end of the first and second Y-shaped adapters contain adjacent first and second methylation-sensitive restriction endonuclease recognition sites, wherein the first site is methylated on both strands on the first adapter and unmethylated on both strands on the second adapter, and wherein the second site on the first adapter is unmethylated on both strands on the first adapter but methylated on both strands on the second adapter, whereby upon formation of the heterohybrids and the homohybrids; the homohybrids are susceptible to digestion with a restriction endonuclease that recognizes the methylation-sensitive restriction endonuclease recognition sites and the heterohybrids are not susceptible to digestion with the restriction endonuclease.

6. The method of claim 5 wherein the restriction endonuclease is MboI.

7. The method of claim 5 wherein the restriction endonuclease is AluI.

8. The method of claim 5 wherein the restriction endonuclease is DpnI.

9. A method to selectively amplify or recover homohybrid or heterohybrid DNA resulting from mixing, denaturating, and reannealing two or more DNA pools, wherein each pool comprises the DNA of a different individual or a mixture of DNA from multiple individuals, comprising:

ligating first Y shaped adapters onto a first pool of restriction endonuclease digested DNA molecules, wherein the first Y shaped adapters comprise a complementary and a non-complementary end, said non-complementary end comprising a 5' terminal sequence of a first DNA strand that is non-complementary to a 3' terminal sequence of a second DNA strand, wherein the 5' terminal sequence is longer than the 3' terminal sequence, wherein the first Y shaped adapters contain a recognition site for a restriction endonuclease in the non-complementary 5' terminal sequence, which restriction endonuclease only cuts double stranded DNA;

ligating second Y shaped adapters onto a second pool of restriction endonuclease digested DNA molecules, Wherein the second Y shaped adapters comprise a complementary and a non-complementary end, said non-complementary end comprising a 5' terminal sequence of a first DNA strand that is non-complementary to a 3' terminal sequence of a second DNA strand, wherein the 5' terminal sequence is longer than the 3' terminal sequence, wherein the second Y shaped adapters contain the recognition site for the restriction endonuclease in the 5' terminal sequence which only cuts double stranded DNA, wherein the 3' terminal sequence of the first Y-shaped adapter is complementary to the 5' terminal sequence of the second Y-shaped adapter and the 3' terminal sequence of the second Y-shaped adapter is complementary to the 5' terminal sequence of the first Y-shaped adapter;

mixing, denaturing and reannealing the first pool ligated to the first adapter with the second pool ligated to the second adapter to form a mixture containing heterohybrids and homohybrids;

extending complementary 3' terminal nucleotides of the heterohybrids using a DNA polymerase that lacks a 3'–5' exonuclease activity to form new 3' ends on the heterohybrids;

contacting the restriction endonuclease with the mixture of heterohybrids and homohybrids, whereby only heterohybrids are cleaved; and recovering said heterohybrids or homohybrids from the mixture of homohybrids and heterohybrids.

10. A method to selectively amplify or recover heterohybrid DNA resulting from mixing, denaturing, and reannealing two or more DNA pools, wherein each of said pools comprises the DNA of a different individual or DNA from multiple individuals, comprising:

ligating first Y shaped adapters onto a first pool of restriction endonuclease digested DNA molecules, wherein the first Y shaped adapters comprise a complementary and a non-complementary end, said non-complementary end comprising a 5' terminal sequence of a first DNA strand that is non-complementary to a 3' terminal sequence of a second DNA strand, wherein the 5' terminal sequence is longer than the 3' terminal sequence;

ligating second Y shaped adapters onto a second pool of restriction endonuclease digested DNA molecules, wherein the second Y shaped adapters comprise a complementary and a non-complementary end, said non-complementary end comprising a 5' terminal sequence of a first DNA strand that is non-complementary to a 3' terminal sequence of a second DNA strand, wherein the 5' terminal sequence is longer than the 3' terminal sequence, wherein the 3' terminal sequence of the first Y shaped adapter is complementary to the 5' terminal sequence of the second Y shaped adapter and the 3' terminal sequence of the second Y shaped adapter is complementary to the 5' terminal sequence of the first Y shaped adapter;

mixing, denaturing and reannealing the first pool ligated to the first adapter with the second pool ligated to the second adapter to form a mixture containing heterohybrids and homohybrids;

extending complementary 3' terminal nucleotides of the heterohybrids using a DNA polymerase that lacks a 3'–5' exonuclease activity and using deoxyribonucleotide triphosphates which are labeled with a capture moiety; and recovering the heterohybrids by contacting the mixture of heterohybrids and homohybrids with an affinity reagent for the capture moiety, whereby the heterohybrids are selectively captured.

11. The method of claim 10 wherein the capture moiety is biotin and the affinity reagent is avidin or strepavidin.

12. The method of claim 10 wherein the capture moiety is an antigen and the affinity reagent is an antibody specific for the antigen.

13. A method of estimating the extent of heterohybrid enrichment resulting from mixing, denaturating, and reannealing two or more DNA pools, wherein each of the pools comprises DNA of a different individual or a mixture of DNA from multiple individuals, comprising:

ligating first Y shaped adapters onto a first pool of restriction endonuclease digested DNA molecules, wherein the first Y shaped adapters comprise a complementary and a non-complementary end, said non-complementary end comprising a 5' terminal sequence of a first DNA strand that is non-complementary to a 3' terminal sequence of a second DNA strand, wherein the 5' terminal sequence is longer than the 3' terminal sequence;

ligating second Y shaped adapters onto a second pool of restriction endonuclease digested DNA molecules, wherein the second Y shaped adapters comprise a complementary and a non-complementary end, said non-complementary end comprising a 5' terminal sequence of a first DNA strand that is non-complementary to a 3' terminal sequence of a second DNA strand, wherein the 5' terminal sequence is longer than the 3' terminal sequence, wherein the 3' terminal sequence of the first Y shaped adapter is complementary to the 5' terminal sequence of the second Y shaped adapter and the 3' terminal sequence of the second Y shaped adapter is complementary to the 5' terminal sequence of the first Y shaped adapter;

mixing, denaturing and reannealing the first pool ligated to the first adapter with said second pool ligated to the second adapter to form a mixture containing heterohybrids and homohybrids;

dividing the mixture containing the heterohybrids and homohybrids into first and second sample portions;

treating the homohybrids and the heterohybrids of the first sample portion with a DNA polymerase that, has 3'–5' exonuclease activity to extend the complementary 3' terminal nucleotides of the heterohybrids and to repair and extend the 3' terminal sequence of the non-complementary end of the homohybrids;

treating the homohybrids and the heterohybrids of the second sample portion with a DNA polymerase that lacks 3'-5' exonuclease activity to extend the complementary 3' terminal nucleotides of the heterohybrids and form new 3' ends;

amplifying the homohybrids and the heterohybrids of the first sample portion using first and second primers complementary to each of the non-complementary 5' ends of the first and the second Y shaped adapters;

amplifying the heterohybrids of the second sample portion using the first and second primers; and comparing the amplified homohybrids and heterohybrids obtained in the first sample portion to the amplified heterohybrids obtained in the second sample portion, whereby an estimate of the extent of heterohybrid enrichment can be obtained.

14. A method to selectively amplify or recover homohybrid DNA resulting from mixing, denaturating, and reannealing two or more DNA pools, wherein each of the pools comprises DNA of different individual or DNA of a mixture from multiple individuals, comprising:

ligating first Y shaped adapters onto a first pool of restriction endonuclease digested DNA molecules, wherein the first Y shaped adapters comprise a complementary and a non-complementary end, said non-complementary end comprising a 5' terminal sequence of a first DNA strand that is non-complementary to a 3' terminal sequence of a second DNA strand, wherein the 5' terminal sequence is longer than the 3' terminal sequence, wherein the first Y shaped, adapter, further comprises a recognition site for a restriction endonuclease that cuts only one strand of a double stranded DNA molecule;

ligating second Y shaped adapters onto a second pool of restriction endonuclease digested DNA molecules, wherein the second Y shaped adapters comprise a complementary and a non-complementary end, said non-complementary end comprising a 5' terminal sequence of a first DNA strand that is non-complementary to a 3' terminal sequence of a second DNA strand, wherein the 5' terminal sequence is longer than the 3' terminal sequence, wherein the second Y shaped adapter further comprises the recognition site for the restriction endonuclease, wherein the 3' terminal sequence of the first Y shaped adapter is complementary to the 5' terminal sequence of the second Y shaped adapter and the 3' terminal sequence of the second Y shaped adapter is complementary to the 5' terminal sequence of the first Y shaped adapter;

mixing, denaturing and reannealing the first pool ligated to the first adapter with the second pool ligated to the second adapter to form a mixture containing heterohybrids and homohybrids;

extending complementary 3' terminal nucleotides of the heterohybrids using a DNA polymerase that lacks a 3'-5' exonuclease activity to form new 3' ends on the heterohybrids;

contacting the restriction endonuclease with the mixture of heterohybrids and homohybrids under conditions where the restriction endoclease makes a single stranded nick;

heating the mixture of heterohybrids and homohybrids to a temperature which will denature the 3' terminal sequences on the homohybrids but which will not denature the extended 3' terminal sequences on the heterohybrids; and amplifying the homohybrid DNA by polymerase chain reaction employing a first primer with the same nucleotide sequence as the non-complementary 5' terminal sequence of the first Y shaped adapters or a second primer with the same nucleotide sequence as the non-complementary 5' terminal sequence of the second Y shaped adapters.

15. The method of claim 14 wherein the restriction endonuclease is N.BstNB1.

16. The method of claim 14 wherein the recognition site for the endonuclease is between 1 and 36 nucleotides of the 3' terminal sequence of the non-complementary end of the first or second Y-shaped adapters and is within the complementary end of said first or second Y-shaped adapters.

17. The method of claim 14 wherein the recognition site for the endonuclease is between 1 and 15 nucleotides of the 3' terminal sequence of the non-complementary end of the first or second Y-shaped adapters and is within the complementary end of said first or second Y-shaped adapters.

18. A method for quantitatively profiling single nucleotide polymorphisms (SNPs) within a first or second DNA pool, or between first and second DNA pools, and quantitatively profiling the perfectly matched (PM) segments within the first or second DNA pool or between the first and second DNA pools wherein each pool comprises DNA of an individual or a mixture from multiple individuals, and the DNA may be from genomic DNA or cDNA or a collection of multiple genes or clones, the method comprising:

digesting first and second DNA pools with a restriction endonuclease (RF) to obtain corresponding first and second restriction fragment (RF) pools;

ligating separately the first and second RF pools to a pair of differentially designed adapters to form a first pool of RF-adapter constructs and a second pool of RF-adapter constructs;

mixing together, denaturing, and reannealing said first pool of RF-adapter constructs with said second pool of RF-adapter constructs to form a mixture containing heterohybrids and homohybrids, the heterohybrids and homohybrids containing PM fragments and mismatch (MM) fragments;

separating and enriching and collecting separately the PM fragments from mismatch (MM) fragments of the mixture;

selectively recovering either heterohybrids or one of the homohybrids, and separately collecting the fragment pools of MM heterohybrids, PM heterohybrids, MM homohybrids of the first pool, PM homohybrids of the first pool, MM homohybrids of the second pool and PM homohybrids of the second pool; and parallelly analyzing a combination of two or more of the fragment pools to extract information of the sequence nature, frequencies, and localizations in the genome.

19. The method according to claim 18 where the adapters ligated to the RE pools are a set of heterohybrid-directed (HeD) adapters or their derivations, wherein the set of HeD adapters comprises a first adapter and a second adapter, each adapter comprises a pair of annealed strands of oligonucleotides that form a complementary and a non-complementary section, the complementary section comprises an appropriate blunt end or a cohesive end with recessed 3' or 5' end for ligating onto the ends of DNA RFs, the 5' end of the complementary section is phosphorylated, the non-complementary section comprises a 5' terminal sequence of a first DNA strand that is not complementary to a 3' terminal sequence of a second DNA strand, the 5' terminal sequence of the non-complementary section is longer than the 3'-terminal sequence, the complementary section of the first and second adapters share their sequences, the non-complementary 5' terminal nucleotides of the first and second adapter are different, the non-complementary 3' terminal nucleotides of the first adapter is complementary to the 5' terminal nucleotides immediately close to the complementary section of the second adapter, and the non-complementary 3' terminal nucleotides of the second adapter is complementary to the 5' terminal nucleotides immediately close to the complementary section of the first adapter.

20. A method for selective recovery of heterohybrids of first and second pools, homohybrids of a first pool, or homohybrids of a second pool resulting from mixing, denaturation and reannealing of two DNA pools, comprising:

(a) digesting first and second DNA pools with a restriction endonuclease (RE) to obtain corresponding first and second restriction fragment (RF) pools;

(b) ligating separately the first and second RF pools to a first HeD adapter and a second HeD adapter to form first and second pools of RF-adapter constructs, wherein each adapter comprises a pair of annealed strands of oligonucleotides that form a complementary and a non-complementary section, the complementary section comprises an appropriate blunt end or a cohesive end with recessed 3' or 5' end for ligating onto the ends of the first and second RF pools, the 5' end of the complementary section is phosphorylated, the non-complementary section comprises a 5' terminal sequence of a first DNA strand that is not complementary to a 3' terminal sequence of a second DNA strand, the 5' terminal sequence of the non-complementary section is longer than the 3'-terminal sequence, the complementary section of the first and second adapters share their sequences, the non-complementary 5' terminal nucleotides of the first and second adapter are different, the non-complementary 3' terminal nucleotides of the first adapter is complementary to the 5' terminal nucleotides immediately close to the complementary section of the second adapter, and the non-complementary 3' terminal nucleotides of the second adapter is complementary to the 5' terminal nucleotides immediately close to the complementary section of the first adapter;

(c) mixing together, denaturing, and reannealing the first pool of RF-adapter constructs with the second pool of RF-adapter constructs to form a mixture containing heterohybrids and homohybrids;

(d) dividing the mixture containing heterohybrids and homohybrids into first and second aliquots, and (e) (i) filling in completely the 3' end of the heterohybrids of the first aliquot with a 3'–5' exonuclease minus DNA polymerase and 4 deoxyribonucleotide triphosphates; and (ii) recovering and amplifying selectively the filled in heterohybrids from the first aliquot with a pair of primers complementary to the two newly extended 3' ends; or (f) (i) using a 3'–5' exonuclease plus DNA polymerase and four deoxyribonucleotide triphosphates to fill in the 3' end of the heterohybrids and the homohybrids of the second aliquot; and (ii) selectively recovering the homohybrids with a primer complementary to the first HeD adapter sequence to recover the homohybrids originally from the first RF pool, or using a primer complementary to the second HeD adapter sequence to recover the homohybrids originally from the second RF pool.

21. A method for selective recovery of heterohybrids of a first and a second pool of DNA, homohybrids of a first pool of DNA, or homohybrids of a second pool of DNA resulting from the mixing, denaturation and reannealing of two DNA pools, comprising:

(a) digesting the first and second DNA pools with a restriction endonuclease (RE) to obtain corresponding first and second restriction fragment (RF) pools;

(b) ligating separately the first and second RF pools to a pair of modified HeD adapters to form first and second pools of RF-adapter constructs, wherein the pair of modified HeD adapters comprises a first modified HeD adapter and a second modified HeD adapter, each adapter comprises a pair of annealed strands of oligonucleotides that form a complementary and a non-complementary section, the complementary section comprises an appropriate blunt end or a cohesive end with recessed 3' or 5' end for ligating onto the ends of the first and second RF pools, the 5' end of the complementary section is phosphorylated, the non-complementary section comprises a 5' terminal sequence of a first DNA strand that is not complementary to a 3' terminal sequence of a second DNA strand, the 5' terminal sequence of the non-complementary section is longer than the 3'-terminal sequence, the complementary section of the first and second adapters share their sequences, the non-complementary 5' terminal nucleotides of the first and second adapter are different, the non-complementary 3' terminal nucleotides of the first adapter is complementary to the 5' terminal nucleotides immediately close to the complementary section of the second adapter, and the non-complementary 3' terminal nucleotides of the second adapter is complementary to the 5' terminal nucleotides immediately close to the complementary section of the first adapter; each of the modified HeD adapters further contains a recognition site for a nicking restriction endonuclease that is capable of cutting only one strand of a double stranded DNA molecule located at the complementary section of the adapter located at the complementary section of the adapter;

(c) mixing together, denaturing, and reannealing the first pool of RF-adapter constructs with the second pool of RF-adapter constructs to form a mixture containing heterohybrids and homohybrids;

(d) filling in completely and selectively the 3' end of the heterohybrids with a 3'–5' exonuclease minus DNA polymerase and dividing the mixture into first and second aliquots;

(e) recovering and amplifying selectively the filled in heterohybrids from the first aliquot with a pair of primers complementary to the two newly extended 3' ends; or (f) (i) contacting the nicking restriction endonuclease with the second aliquot under conditions where it makes a single stranded nick;

(ii) heating the contacted second aliquot to a temperature which releases the short 3' terminal sequences of the homohybrids resulting from step (f)(i), but which does not release internal fragments between the adapters;

(iii) ligating every gap of the internal fragments in the nucleotides between the adapters with a Taq ligase; and (iv) recovering selectively the homohybrids with a first primer complementary to the first modified HeD adapter or a second primer complementary to the second modified HeD adapter.

22. The method of claim 21 wherein the restriction endonuclease is N.BstNB I.

23. A method for selective recovery of heterohybrids of a first and a second pool of DNA, homohybrids of the first pool of DNA, or homohybrids of the second pool of DNA resulting from the mixing, denaturation and reannealing of first and second DNA pools, comprising:

(a) digesting first and second DNA pools with a first restriction endonuclease (RE) to obtain first and second restriction fragment (RF) pools;

(b) ligating the first and second RF pools to first and second modified HeD adapters to form first and the second pools of RF-adapter constructs, wherein each adapter comprises a pair of annealed strands of oligonucleotides that form a complementary and a non-complementary section, the complementary section comprises an appropriate blunt end or a cohesive end with recessed 3' or 5' end for ligating onto the ends of the first and second RF pools, the 5' end of the complementary section is phosphorylated, the non-complementary section comprises a 5' terminal sequence of a first DNA strand that is not complementary to a 3' terminal sequence of a second DNA strand, the 5' terminal sequence of the non-complementary section is longer than the 3'-terminal sequence, the complementary section of the first and second adapters share their sequences, the non-complementary 5' terminal nucleotides of the first and second adapter are different, the non-complementary 3' terminal nucleotides of the first adapter is complementary to the 5' terminal nucleotides immediately close to the complementary section of the second adapter, and the non-complementary 3' terminal nucleotides of the second adapter is complementary to the 5' terminal nucleotides immediately close to the complementary section of the first adapter; and wherein each of the modified HeD adapters further contains a recognition site for a second restriction endonuclease that is sensitive to methylated nucleotide and cleaves DNA duplexes in which both strands are methylated at specific nucleotides, the recognition site being located in the adapter at the 5' terminal sequence of the non-complementary section;

(c) mixing together, denaturing, and reannealing the first pool of RF-adapter constructs with the second pool of RF-adapter constructs to form a mixture containing heterohybrids and homohybrids;

(d) filling in completely and selectively the 3' end of the heterohybrids with a 3'–5' exonuclease minus DNA polymerase and four standard dNTPs; and purifying the filled-in heterohybrid mixture, especially removing the free dNTPs;

(e) filling in selectively the 3' end of the constructs of only homohybrids with a 3'–5' exonuclease plus DNA polymerase in the presence of 4 dNTPs wherein selected dNTP(s) are methylated to form filled-in homohybrids that contain a recognition site of the second restriction endonuclease, and dividing the filled-in homohybrid and heterohybrid mixture into first and second aliquots;

(f) recovering selectively the homohybrids of the first aliquot by amplifying with a primer complementary to the first adapter sequence or a primer complementary to the second adapter sequence; or (g) (i) contacting the second restriction endonuclease with the second aliquot under conditions where the second restriction endonuclease cuts off the 5' terminal sequence of the adapters of the homohybrid constructs;

(ii) filling in the 3' end newly generated by the second restriction endonuclease in step (g)(i); and (iii) recovering and amplifying selectively the heterohybrids with primers complementary to the newly filled-in 3' ends.

24. A method for selective recovery of heterohybrids or either one of the homohybrids resulting from the mixing, denaturation and reannealing of first and second DNA pools, comprising:

(a) digesting the first and second DNA pools with a first restriction endonuclease (RE) to obtain their corresponding first and second restriction fragment (RF) pools;

(b) ligating separately the pair of RF pools to a pair of modified HeD adapters to form the first and the second pools of RF-adapter constructs, wherein the pair of HeD adapters comprises a first adapter and a second adapter, each adapter comprises a pair of annealed strands of oligonucleotides that form a complementary and a non-complementary section, the complementary section comprises an appropriate blunt end or a cohesive end with recessed 3' or 5' end for ligating onto the ends of DNA RFs, the 5' end of the complementary section is phosphorylated, the non-complementary section comprises a 5' terminal sequence of a first DNA strand that is not complementary to a 3' terminal sequence of a second DNA strand, the 5' terminal sequence of the non-complementary section is longer than the 3'-terminal sequence, the complementary section of the first and second adapters share their sequences, the non-complementary 5' terminal nucleotides of the first and second adapter are different with sequence alpha and sequence beta respectively, the non-complementary 3' terminal nucleotides of the first adapter complementary to the 5' terminal nucleotides is immediately close to the complementary section of the second adapter, and the non-complementary 3' terminal nucleotides of the second adapter is complementary to the 5' terminal nucleotides is immediately close to the complementary section of the first adapter; wherein each of the modified HeD adapters further contains a recognition site for a second restriction endonuclease that is capable of cutting a DNA duplex that both strands are methylated at specific nucleotide(s), and this site being located at the 5' free terminal section of the RF-adapter constructs; and wherein the each of the modified HeD adapters further contains a recognition site for a nicking restriction endonuclease that is capable of cutting only one strand of a double stranded DNA molecule, and this site being located at the complementary section of the adapter;

(c) mixing together, denaturing, and reannealing the said first pool of RF-adapter constructs with the said second pool of RF-adapter constructs to form a mixture containing heterohybrids and homohybrids;

(d) filling in completely and selectively the 3' end of heterohybrids in the mixture with a 3'–5' exonuclease minus DNA polymerase and four standard dNTPs, and purifying the resulted mixture and completely removing the left free dNTPs;

(e) contacting the said nicking restriction endonuclease with the mixture of heterohybrids and homohybrids under conditions where it makes a single stranded nick;

f) heating the DNA mixture to a temperature that causes the 3' ends of the homohybrids that is not extended to dissociate from the adapters, but does not cause the 3' end of the homohybrids to dissociated, and treating the mixture with a ligase to close every nick in every internal fragment;

(g) filling in the 3' end of the constructs of the homohybrids in the mixture with a 3'–5' exonuclease plus DNA polymerase, in the presence of 4 dNTPs with selective dNTP(s) being methylated to generate homohybrids containing the recognition site of the second restriction endonuclease, and dividing the mixture into first and second aliquots; and (h) recovering selectively from the first aliquot of mixture the homohybrids from the first pool using a first primer complementary to sequence alpha of the first adapter or the homohybrids from the second pool using a primer complementary to sequence beta of the second adapter; or (i) (i) contacting the second restriction endonuclease with the second aliquot of the mixture of heterohybrids and homohybrids under conditions where it cuts off the distal part of the adapters from two homohybrid constructs;

(ii) filling in the 3' termini of homohybrid constructs newly generated in step (i)(i); and (iii) recovering and amplifying selectively the heterohybrids from the second aliquot with a pair of primers complementary to the two newly extended 3' ends.

25. A method for selective recovery of heterohybrids of a first and a second DNA pool, or homohybrids of the first DNA pool, or homohybrids of the second DNA pool resulting from the mixing, denaturation and reannealing of the two DNA pools comprising:

(a) digesting the first and second DNA pools with a first restriction endonuclease (RE) to obtain first and second restriction fragment (RF) pools;

(b) ligating the first and second RF pools to first and second modified HeD adapters to form first and second pools of RF-adapter constructs, wherein the first and second modified HeD adapters contain a first and a second adjacent nucleotide-methylation-sensitive restriction endonuclease recognition sites located in the complementary portion of the first nucleotide-methylation sensitive site is methylated on both strands of the first adapter but unmethylated on both strands of the second adapter, the second nucleotide methylation sensitive site is unmethylated on both strands of the first adapter but methylated on both strands of the second adapter, whereby upon formation of heterohybrids and homohybrids by denaturing and reannealing, the homohybrids are susceptible to digestion by a second restriction endonuclease that is methylation sensitive, but the heterohybrids are not susceptible to digestion by the second restriction endonuclease;

(c) mixing together, denaturing, and reannealing the first pool of RF-adapter constructs with the second pool of RF-adapter constructs to form a mixture containing heterohybrids and homohybrids;

(d) filling in the 3' end of the heterohybrids and homohybrids with a DNA polymerase in the presence of four deoxyribonucleotide triphosphates and dividing the mixture into first and second aliquots; and (e) (i) contacting the second methylation sensitive restriction endonuclease with the first aliquot under conditions where the second restriction endonuclease cuts off the distal part of the adapter from the homohybrid constructs; and (ii) recovering and amplifying selectively the uncut constructs; or (f) recovering selectively the homohybrids by amplifying the second aliquot with a primer complementary to the first modified HeD adapter or a primer complementary to the second modified HeD adapter.

26. The method of claim 24 wherein the restriction endonuclease is DpnI.

27. The method of claim 24 wherein the restriction endonuclease is TaqI.

28. The method of claim 24 wherein the restriction endonuclease is MboI.

29. A method wherein a pair of modified HeD adapters is used for selective recovery of heterohybrids of a first and a second DNA pool, or homohybrids of the first DNA pool, or homohybrids of the second DNA pool resulting from the mixing, denaturation and reannealing of the first and second DNA pools;

(a) digesting the first and second DNA pools with a restriction endonuclease (RE) to obtain first and second restriction fragment (RF) pools;

(b) ligating separately the first and second RF pools to first and second modified HeD adapters to form first and second pools of RF-adapter constructs, wherein the 5' free terminal ends of the first and second modified HeD adapters are separately attached to first and second capture moieties, and wherein each adapter does not have a 3' overhang and the entire shorter strand is completely complementary to a portion of the longer strand of the adapter, whereby upon formation of heterohybrids and homohybrids by denaturing and reannealing, the homohybrids are attached to the first capture moiety or the second capture moiety, and the heterohybrids are attached to both the first capture moiety and the second capture moiety;

(c) mixing together, denaturing, and reannealing the first pool of RF-adapter constructs with the second pool of RF-adapter constructs to form a mixture heterohybrids and homohybrids;

(d) filling in the 3' end of the heterohybrids and homohybrids with a DNA polymerase in the presence of 4 deoxyribonucleotide triphosphates to form filled-in homohybrids and heterohybrids;

(e) recovering the filled-in heterohybrids by capturing the first moiety with a first affinity reagent followed by capturing the second moiety with a second affinity reagent, captured heterohybrids being able to be amplified with a pair of primers complementary to the two newly filled-in 3' ends; or (f) (i) recovering the homohybrids of the first DNA pool by removing the homohybrids and heterohybrids attached to the second moiety with the second affinity reagent and capturing the first moiety with the first affinity reagent; the homohybrids of the first pool being capable of being amplified with a primer complementary to the newly filled-in 3' ends of the homohybrids of the first DNA pool; or (ii) recovering the homohybrids of the second pool by removing the homohybrids and heterohybrids attached to the first moiety with the first affinity reagent and capturing the second moiety with the second affinity reagent; the homohybrids of the second pool being capable of being amplified with a primer complementary to the newly filled-in 3' ends of the second homohybrids.

30. The method of claim 29 wherein the first capture moiety is biotin and the first affinity reagent is avidin or strepavidin, and the second capture moiety is digoxigenin and the second affinity is anti-digoxigenin antibody.

31. A method for efficient and selective recovery of fully reannealed DNA fragments resulting from the denaturation and reannealing of a DNA pool, comprising:

(a) digesting a DNA pool with a restriction endonuclease (RE) to obtain its restriction fragment (RF) pool;

(b) denaturing, and reannealing the RF pool;

(c) ligating the RF pool to an adapter having a long and a short oligonucleotide annealed to each other, of which the 5' end of the long oligonucleotide is not adjacent to the restriction fragments of the restriction fragment pool, and wherein the 5' end of the short oligonucleotide is ligated to the restriction fragments of the restriction fragment pool;

(d) adding Taq polymerase to the mixture in the presence of four deoxyribonucleotide triphosphates and filling the end of the RF-adapter construct formed in step (c); and (e) recovering and amplifying the filled-in constructs with a pair of primers complementary to the two newly extended 3' ends.

32. The methods according to any one of claim 25–29 or 46 wherein the modified HeD adapters comprise two frilly complementary oligonucleotides, wherein the 5' end of the oligonucleotide ligated to the restriction fragment is phosphorylated.

33. A method wherein first and second adapters are used for selective recovery of heterohybrids resulting from the mixing, denaturation and reannealing of first and second DNA pools, comprising:

(a) digesting a first and a second DNA pool with a restriction endonuclease (RE) to obtain first and second restriction fragment pools;

(b) ligating separately the first and second RF pools to first and second HeD adapters to form first and second pools of RF-adapter constructs, wherein the first and second HeD adapters comprise different sequences, wherein the first and second HeD adapters each comprises a long and a short oligonucleotide annealed to each other, the 5' end of the long oligonucleotide is single stranded and is not adjacent to the restriction fragments of the restriction fragment pool, and the 5' end of the short oligonucleotide is adjacent to the restriction fragments of the restriction fragment pool and is free of a phosphorylation group;

(c) denaturing, and reannealing the first and second pools of RF-adapter constructs to form a mixture of reannealed RF-adapter constructs;

(d) adding Taq polymerase to the mixture in the presence of four deoxyribonucleotide triphosphates and filling the end of the reannealed RF-adapter constructs to form filled-in constructs; and (e) recovering and amplifying the filled-in constructs with a pair of primers complementary to the two different newly extended 3' ends.

34. The methods according to any one of claim 18, 20–28, 31, or 33 wherein the steps of recovering or selectively recovering are performed by polymerase chain reaction (PCR).

35. The methods according to any one of claim 18, 20–28, 31 or 33 wherein the steps of recovering or selectively recovering are performed by rolling cycle amplification (RCA).

36. The method according to claim 18 wherein the separation and enrichment of mismatch fragments (MM) or perfectly matched fragments (PM) from the mixture comprising:

contacting a DNA glycosylase or another DNA mismatch repair enzyme with a DNA mixture of PM fragments or constructs and MM fragments or constructs under conditions wherein the DNA glycosylase or the other DNA mismatch repair enzyme removes the mismatched nucleotide from the MM fragment, leaving an abasic site and an associated aldehyde in one strand or two strands of the duplex, and nicking at the abasic site; and recovering the DNA fragments containing the abasic site as MM fragments.

37. The method according to claim 18 wherein the separating and enriching and collecting separately the PM fragments from the mismatch fragments (MM) from the mixture comprises:

contacting a DNA mismatch repair enzyme with the mixture of PM fragments and MM fragments under conditions wherein the DNA mismatch repair enzyme removes a mismatched nucleotide from the MM fragment and leaves an abasic site and an associated aldehyde in one strand or two strands of the MM fragment but does not cleave the resulting MM fragment;

separating the mixture of PM and MM fragments into a first fraction which is bound to the DNA mismatch repair enzyme and a second fraction which is not bound to the DNA mismatch repair enzyme, and releasing and enriching the first fraction for the MM fragments.

38. The method according to claim 37 wherein the DNA mismatch repair enzyme is a DNA Glycosylase that recognizes the MM fragment, generates an abasic site and binds to the abasic sites of the MM fragments in the presence of EDTA that withdraws $Mg^{2+}$ from a reaction buffer.

39. The method according to claim 37 wherein the DNA mismatch repair enzyme is a DNA glycosylase that is immobilized on a solid matrix, wherein the mixture of PM and MM fragments is separated by washing the PM fragment off the solid matrix but retaining the MM fragments on the solid matrix, and wherein the MM fragments bound to the DNA glycosylase are then eluted from the solid matrix in the presence of $Mg^{2+}$, or the complex of DNA glycosylase with DNA fragments are eluted from the solid matrix.

40. The method according to claim 18 wherein the separating and enriching and collecting separately the PM fragments from the mismatch fragments (MM) of the mixture comprises:

contacting a DNA mismatch repair enzyme with the mixture of PM fragments and MM fragments under conditions wherein the DNA mismatch repair enzyme removes a mismatched nucleotide from the MM fragments and leaves an abasic site and an associated aldehyde in one strand or two strands of the MM fragments but does not cleave or bind to the resulting MM fragments; and applying an immobilized-chemical molecule to bind specifically to the abasic site-associated aldehyde in the MM fragments and separating the MM fragments from the free PM fragments.

41. The method of claim 40 wherein the chemical molecule is a hydroxylamine or hydrazide derivative, which forms a stable oxime bond with open-chain aldehydes generated upon abasic site formation.

42. The methods according to any one of claims 37 to 40 wherein the DNA mismatch repair enzyme is thymine DNA glycosylase.

43. The method according to claim 42 wherein the thymine DNA glycosylase is *E. coli* MutY that is capable of recognizing and binding to the MM fragments at the mismatch nucleotide in the presence of sodium borohydride ($NaBH_4$) to produce covalent protein-DNA complex.

44. The method according to claim 18 wherein the selectively recovered PM homohybrids from the first pool, PM homohybrids from the second pool, the MM homohybrids from the first pool, MM homohybrids from the second pool, the PM heterohybrids, and the MM heterohybrids, are analyzed at least partially via microarray hybridization, gel display, subtractive hybridization or representative differential analysis, or FISH (fluorescent in situ hybridization).

45. The method of claim 39 wherein the solid matrix is resin, agarose or beads.

46. The method of claim 45 wherein the beads are magnetic beads.

47. The method of claim 39 wherein the DNA glycosylase is immobilized to the solid matrix via GST or His6.

* * * * *

UNITED STATES PATENT AND TRADEMARK OFFICE
CERTIFICATE OF CORRECTION

PATENT NO. : 6,924,104 B2 Page 1 of 1
DATED : August 2, 2005
INVENTOR(S) : Sherman Weissman et al.

It is certified that error appears in the above-identified patent and that said Letters Patent is hereby corrected as shown below:

Column 25,
Line 49, "Wherein" should read as -- wherein --.

Column 28,
Line 56, "(RF)" should read as -- (RE) --.

Column 29,
Line 14, "(RE)" should read as -- (RF) --.

Column 30,
Lines 64-65, "located at the complementary section" is duplicative and should be deleted.

Column 31,
Line 64, "nucleotide" should read as -- nucleotides --.

Column 33,
Lines 14-15, "end of heterohybrids" should read as -- end of the heterohybrids --.
Line 26, "dissociated" should read as -- dissociate --.

Column 35,
Line 48, "frilly" should read as -- fully --.

Column 37,
Line 17, "methods" should read as -- method --.

Signed and Sealed this

Twenty-fifth Day of October, 2005

JON W. DUDAS
*Director of the United States Patent and Trademark Office*